(12) United States Patent  (10) Patent No.: US 6,942,675 B1
Vargas  (45) Date of Patent: Sep. 13, 2005

(54) TOOL FOR PERFORMING END-TO-END ANASTOMOSIS

(75) Inventor: Jaime S. Vargas, Menlo Park, CA (US)

(73) Assignee: Cardica, Inc., Redwood City, CA (US)

( * ) Notice: Subject to any disclaimer, the term of this patent is extended or adjusted under 35 U.S.C. 154(b) by 557 days.

(21) Appl. No.: 10/159,838

(22) Filed: May 31, 2002

Related U.S. Application Data

(63) Continuation-in-part of application No. 10/083,235, filed on Feb. 26, 2002.

(51) Int. Cl.[7] .............................................. A61B 17/08
(52) U.S. Cl. .................... 606/153; 606/219; 227/175.1
(58) Field of Search .............................. 606/72, 73, 75, 606/120, 213–217, 219–226, 153, 157, 158, 606/222, 151; 424/422, 423; 411/457; 227/175.1, 227/179.1, 180.1

(56) References Cited

U.S. PATENT DOCUMENTS

| | | | |
|---|---|---|---|
| 1,151,300 A | 8/1915 | Soresi | |
| 1,217,637 A | 2/1917 | Rink | |
| 3,048,177 A | 8/1962 | Takaro | |
| 3,114,367 A * | 12/1963 | Carpenter et al. | .......... 606/151 |
| 3,254,650 A | 6/1966 | Collito | |
| 3,254,651 A | 6/1966 | Collito | |
| 3,265,069 A | 8/1966 | Healey, Jr. et al. | |
| 3,519,187 A | 7/1970 | Kapitanov | |
| 3,774,615 A | 11/1973 | Lim et al. | |
| 3,911,926 A | 10/1975 | Peters | |
| 4,245,638 A | 1/1981 | Lebeck | |
| 4,350,160 A | 9/1982 | Kolesov et al. | |
| 4,523,592 A | 6/1985 | Daniel | |
| 4,553,542 A | 11/1985 | Schenck et al. | |
| 4,593,693 A | 6/1986 | Schenck | |
| 4,607,637 A | 8/1986 | Berggren et al. | |
| 4,624,255 A | 11/1986 | Schenck et al. | |
| 4,624,257 A | 11/1986 | Berggren et al. | |
| 4,635,636 A | 1/1987 | Goldstein | |
| 4,657,019 A | 4/1987 | Walsh et al. | |
| 4,721,109 A | 1/1988 | Healey | |
| 4,747,407 A | 5/1988 | Liu et al. | |
| 4,809,695 A * | 3/1989 | Gwathmey et al. | ...... 227/175.1 |
| 4,907,591 A | 3/1990 | Vasconcellos et al. | |
| 4,917,087 A | 4/1990 | Walsh et al. | |
| 4,917,090 A | 4/1990 | Berggren et al. | |
| 4,917,091 A | 4/1990 | Berggren et al. | |
| 5,011,487 A | 4/1991 | Shichman | |
| 5,119,983 A | 6/1992 | Green et al. | |
| 5,141,516 A | 8/1992 | Detweiler | |

(Continued)

FOREIGN PATENT DOCUMENTS

EP  00/15144  3/2000

(Continued)

OTHER PUBLICATIONS

Wood, Michael B. Atlas of Reconstructive Microsurgery 1990 p4-5.

(Continued)

*Primary Examiner*—Julian W. Woo
(74) *Attorney, Agent, or Firm*—Brian A. Schar

(57) ABSTRACT

A tool for performing anastomosis connects two tissue structures end-to-end. A clamp holds each tissue structure. The clamps are movable relative to one another, and are registered together such that the flaps of one tissue structure are pressed against the corresponding flaps of the other tissue structure when the clamps come together. Each flap of one tissue structure is connected to a corresponding flap on the other corresponding tissue structure with at least one connector.

15 Claims, 17 Drawing Sheets

U.S. PATENT DOCUMENTS

| | | | |
|---|---|---|---|
| 5,158,567 A | | 10/1992 | Green |
| 5,192,289 A | | 3/1993 | Jessen |
| 5,462,555 A | * | 10/1995 | Bolanos et al. ............. 606/120 |
| 5,465,894 A | * | 11/1995 | Clark et al. .............. 227/175.1 |
| 5,669,918 A | | 9/1997 | Balazs et al. |
| 5,702,048 A | | 12/1997 | Eberlin |
| 5,897,562 A | * | 4/1999 | Bolanos et al. ............. 606/139 |
| 5,925,052 A | * | 7/1999 | Simmons .................... 606/120 |
| 6,468,285 B1 | | 10/2002 | Hsu et al. |

FOREIGN PATENT DOCUMENTS

WO            99/11178         3/1999

OTHER PUBLICATIONS

Lorenzetti, Fulvio Blood Flow in Free Microvascular Flaps, 2001, p5-52.

* cited by examiner

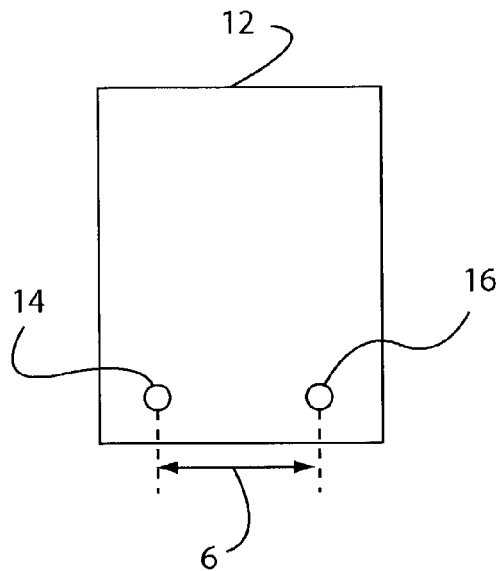
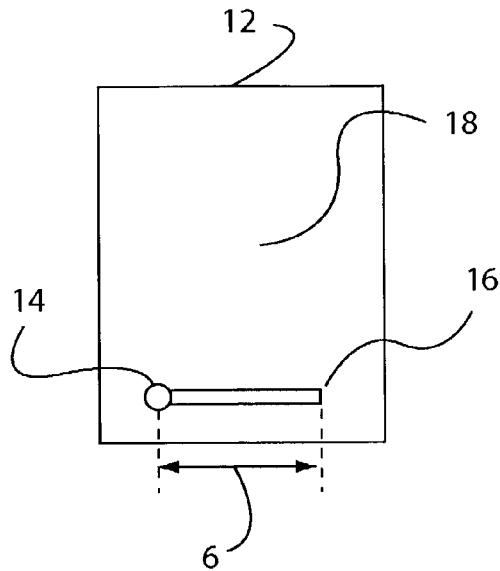
FIG. 2　　　　　　　　FIG. 3
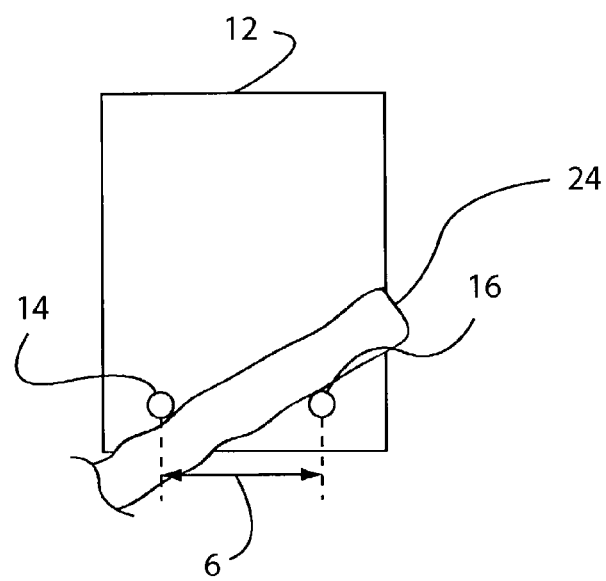
FIG. 4

TOOL FOR PERFORMING END-TO-END ANASTOMOSIS

This patent application is a continuation-in-part of U.S. patent application Ser. No. 10/083,235 filed Feb. 26, 2002.

FIELD OF THE INVENTION

The present invention relates generally to anastomosis, and more particularly to a tool for performing end-to-end anastomosis.

BACKGROUND

End-to-end anastomosis is a surgical procedure for connecting an end of one hollow tissue structure to an end of another hollow tissue structure, such that the spaces within each hollow tissue structure are connected. End-to-end anastomosis is commonly performed in a microvascular context. Microvascular anastomosis is performed between ends of blood vessels in the course of, for example, reattaching severed body parts and/or transplanting organs. The blood vessels connected together often have different diameters, both of which are very small, on the order of one millimeter. Microvascular anastomosis is often performed by hand under a microscope, and is tedious and painstaking work. As a result, it can take many hours to complete just the microvascular anastomosis required to reconnect a severed body part or transplant an organ.

One attempt to provide a mechanism for performing such a microvascular anastomosis is the Microvascular Anastomotic Coupler System from Bio-Vascular, Inc. In this mechanism, an end of each vessel to be connected is everted over a ring with a forceps or similar instrument. Each ring includes a number of pins over which the vessel is everted. The rings are then pressed together, such that the pins on each ring enter recesses in the other ring, connecting the rings and holding the ends of the vessels together. However, this system is limited to use with two blood vessels having substantially the same diameter. Further, manual eversion of a blood vessel having a diameter on the order of one millimeter is difficult and painstaking, particularly when the eversion is to be substantially even around the circumference of the ring. Further, the rings provide a noncompliant anastomosis between the two vessels.

SUMMARY

An anastomosis tool is used to connect two tissue structures end-to-end.

In one aspect of the invention, an end of a tissue structure is sized to a known interface dimension with a tissue preparation device. The tissue preparation device may include a pin and a measuring feature relative to the pin. The measuring feature is configured to measure the interface dimension. A tissue structure is moved relative to the pin until the measuring feature maps the interface dimension onto a cross-section of the tissue structure. The tissue structure is then held in place while two or more cuts are made in it to create at least two flaps at its end.

In another aspect of the invention, an anastomosis tool includes a clamp corresponding to each tissue structure. A tissue preparation device may be integrated with each clamp. The clamps are moveable relative to one another in order to bring the flaps of one tissue structure in contact with the flaps of the other tissue structure. At least one clamp includes at least one connector deployer. Additionally, at least one clamp may include a connector receiver corresponding to a connector deployer on another clamp.

In another aspect of the invention, the flaps on each tissue structure are held by one or more clips. The clip or clips may be provided as a component of each clamp, or may be separate structures or mechanisms detachable from the clamps. By holding the flaps in a predetermined position, the flaps on different tissue structures can be brought together in a configuration suitable for connecting them together.

In another aspect of the invention, at least one clamp is movable relative to a jig. The jig guides the clamps together such that the flaps of one tissue structure are registered against the corresponding flaps of the other tissue structure. The jig may include one or more rails along which at least one clamp is configured to slide.

In another aspect of the invention, each flap of one tissue structure is connected to a corresponding flap on the other corresponding tissue structure with at least one connector. These connectors may be staples or other fasteners. The connectors are spaced apart from one another a distance comparable to the distance between stitches in a sutured anastomosis. By using a number of spaced-apart connectors such as staples, the anastomosis is compliant.

In another aspect of the invention, the anastomosis tool is configured for one-handed operation in order to simplify its use.

In another aspect of the invention, the connectors are positioned initially at least partly within a channel through which an actuator translates. The actuator is translated along the channel to contact each connector in turn, deploying the connectors sequentially. This deployment may be performed by sequentially pushing each connector through an adjacent passage.

In another aspect of the invention, the connectors are positioned initially at least partly within a channel through which an actuator translates. The actuator is translated within the channel to contact and deploy substantially all connectors at substantially the same time. This deployment may be performed by substantially simultaneously pushing each connector through an adjacent passage.

In another aspect of the invention, each clamp includes two arms moveable relative to one another. One arm includes a catch and the other arm includes an aperture or other structure or mechanism configured to engage the catch when the clamp is closed. The engagement between the catch and the aperture holds the clamp in a closed position, trapping a tissue structure within the catch.

In another aspect of the invention, one clamp may be connected to a first member and the other clamp may be connected to a second member. The members may be connected to a trigger and are movable relative to one another, such that the members move closer to one another when the trigger is depressed. Advantageously, the members and trigger are configured such that the anastomosis tool can be held in one hand, and the trigger can be depressed with a single finger or thumb for ease of use.

In another aspect of the invention, the trigger includes or is connected to a crossbar that rotates relative to an axis on one of the members. The crossbar engages at least one actuator, which in turn acts to deploy one or more connectors from at least one arm. The connectors connect the flaps of adjoining tissue structures, thereby creating an anastomosis between those tissue structures.

In another aspect of the invention, the catch is moved out of engagement with the aperture after the anastomosis is complete. he tissue structure is compressed within the clamp, such that moving the catch out of engagement with the aperture causes the clamp to open at least party, freeing the tissue structure.

In another aspect of the invention, at least one of the clamps is detachable from the remainder of the anastomosis tool. A portion of the anastomosis tool thus may be reused for on the same patient, or sterilized and reused on a different patient. A new clamp or clamps may then be connected thereto. In this way, clamps can be rapidly switched when performing several anastomoses on a single patient, and fresh, sterile clamps can be provided for each different patient without having to replace the entire anastomosis tool.

In another aspect of the invention, the connectors used with the anastomosis tool have legs that are beveled at their free ends. The bevel surface of each leg may be oriented such that the bevel surfaces are neither parallel nor coplanar. A number of identical connectors may be deployed by the anastomosis tool to perform a single anastomosis, or different types of staples may be utilized.

BRIEF DESCRIPTION OF THE DRAWINGS

FIG. 2 is a schematic view of one configuration of a tissue preparation device.

FIG. 3 is a schematic view of another configuration of a tissue preparation device.

FIG. 4 is a schematic view of the tissue preparation device of FIG. 3 as used to map the interface length onto the end of a tissue structure.

The use of the same reference symbols in different figures indicates similar or identical items.

DETAILED DESCRIPTION

Figure 1:
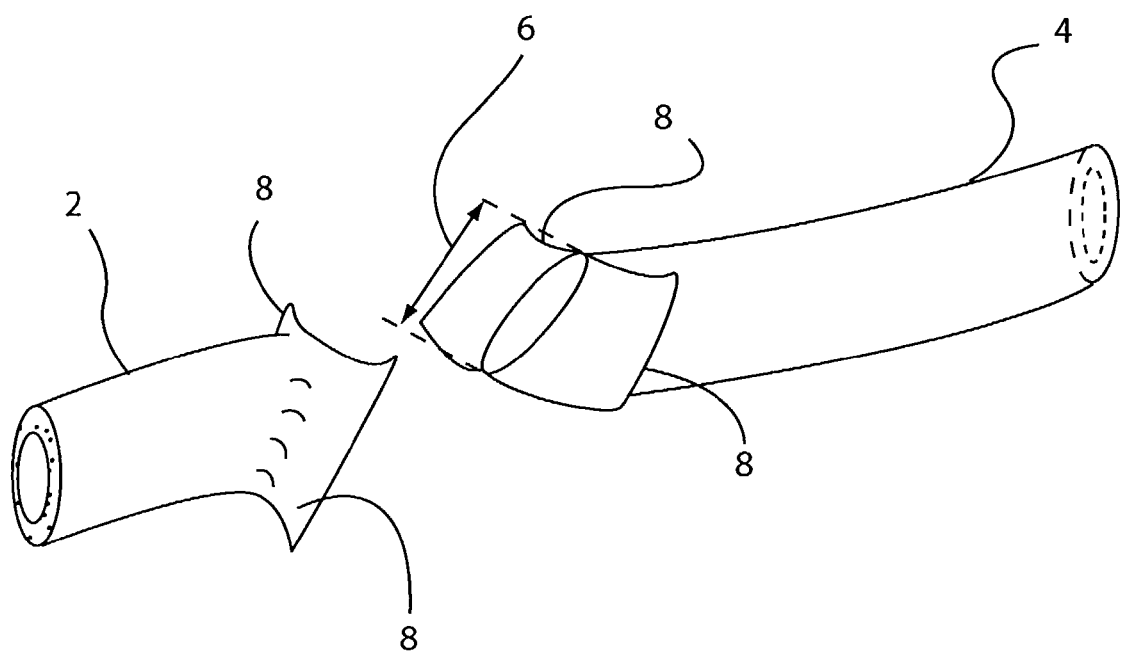
FIG. 1 is a perspective view of two tissue structures to be connected to one another.

Referring to FIG. 1, a first tissue structure 2 and a second tissue structure 4 are to be connected to one another. The tissue structures 2, 4 are hollow structures each having an end in proximity to an end of the other. The tissue structures 2, 4 may be blood vessels, ducts or other tubular structures. For example, these tissue structures 2, 4 may be small blood vessels on the order of one millimeter in diameter, such that the connection between them may be categorized as microvascular anastomosis. Such microvascular anastomosis may be used to connect tissue structures 2, 4 in the course of a transplant procedure, the reattachment of a severed limb or bodily part, or in other contexts.

The first tissue structure 2 may have a different diameter than the second tissue structure 4. Where an organ is being transplanted, the first tissue structure 2 and the second tissue structure 4 may have different diameters because each is from a different individual or from a different part of the same individual, or because a portion of a previous unitary tissue structure was destroyed or damaged. In order to connect tissue structures 2, 4 having different diameters, an interface length 6 is defined and mapped onto the end of each tissue structure 2, 4. The process of determining a cross-section of the tissue structure 2, 4 that has a width substantially equal to the interface length 6 may be referred to as mapping the interface length 6 onto the tissue structure 2, 4. The interface length 6 is defined along an angle to the centerline of each tissue structure 2, 4. The angle at which the end of each tissue structure 2, 4 is cut may be different in order to produce the same interface length 6 at the end of each tissue structure. The end of each tissue structure 2, 4 is cut along that angle, such that the end of each tissue structure 2, 4 defines a plane relative to its centerline. The diameter of the lumen of each tissue structure 2, 4 as measured in that plane is substantially the same. The tissue structures 2, 4 may be flattened while the interface length 6 is mapped onto them, such that the flattened tissue structures 2, 4 are each cut to the interface length 6. The resulting diameter of each tissue structure 2, 4 after returning to its normal, non-flattened state is thus substantially the same, and is slightly less than the interface length 6.

After anastomosis, the centerline of the first tissue structure 2 may be angled relative to the centerline of the second tissue structure 4, because the angle cut at the end of each tissue structure 2, 4 may be different. Advantageously, the interface length 6 is selected to be greater than the expected diameter of either tissue structure 2, 4, such that the end of each tissue structure 2, 4 is cut at an angle to its centerline in order to increase the surface area of the flaps 8. However, the interface length 6 instead may be selected to be closer to the expected diameter of either tissue structure 2, 4.

Referring to FIG. 2, the end of each tissue structure 2, 4 is cut to a width substantially equal to the interface length 6 using a tissue preparation device 12. The tissue preparation device 12 may be integrated into a deployment tool, as described below, or may be an independent mechanism. The tissue preparation device 12 includes a pin 14 extending outward from a surface 18. Alternately, a structure other than a pin 14 could be used. The tissue preparation device 12 also includes a measuring feature 16 spaced apart from the pin 14 a distance substantially equal to the interface length 6. Referring to FIG. 2, the measuring feature 16 is another pin. Referring to FIG. 3, the measuring feature 16 is a visually-perceptible feature on the surface 18. The visually perceptible feature may be a colored strip, a set of ruled lines, or any other visible feature on the surface 18. The visually perceptible feature may be defined on, attached to or otherwise placed on the surface 18. The measuring feature 16 may be any other structure or mechanism useful in measuring the width of a tissue structure 2, 4.

Referring to FIG. 4, a tissue structure 2, 4 is measured using the tissue preparation device 12 of FIG. 2. The tissue structure 2, 4 is placed between the pin 14 and the measuring feature 16, using a forceps or other tool, or by hand. The tissue structure 2, 4 is then moved relative to both the pin 14 and the measuring feature 16 such that, as viewed from the top, one side of the tissue structure 2, 4 contacts the pin 14 and the opposite side of the tissue structure 2, 4 contacts the measuring feature 16. The distance between these two points of contact is substantially equal to the interface length 6. The interface length 6 is potentially a greater distance than the width of the tissue structure 2, 4. Thus, the tissue structure 2, 4 is moved to an angle to an imaginary line connecting the pin 14 and the measuring feature 16, such that adequate tissue is present between the pin 14 and the measuring feature 16 to allow the interface length 6 to be mapped onto that tissue structure 2, 4.

Figure 5:
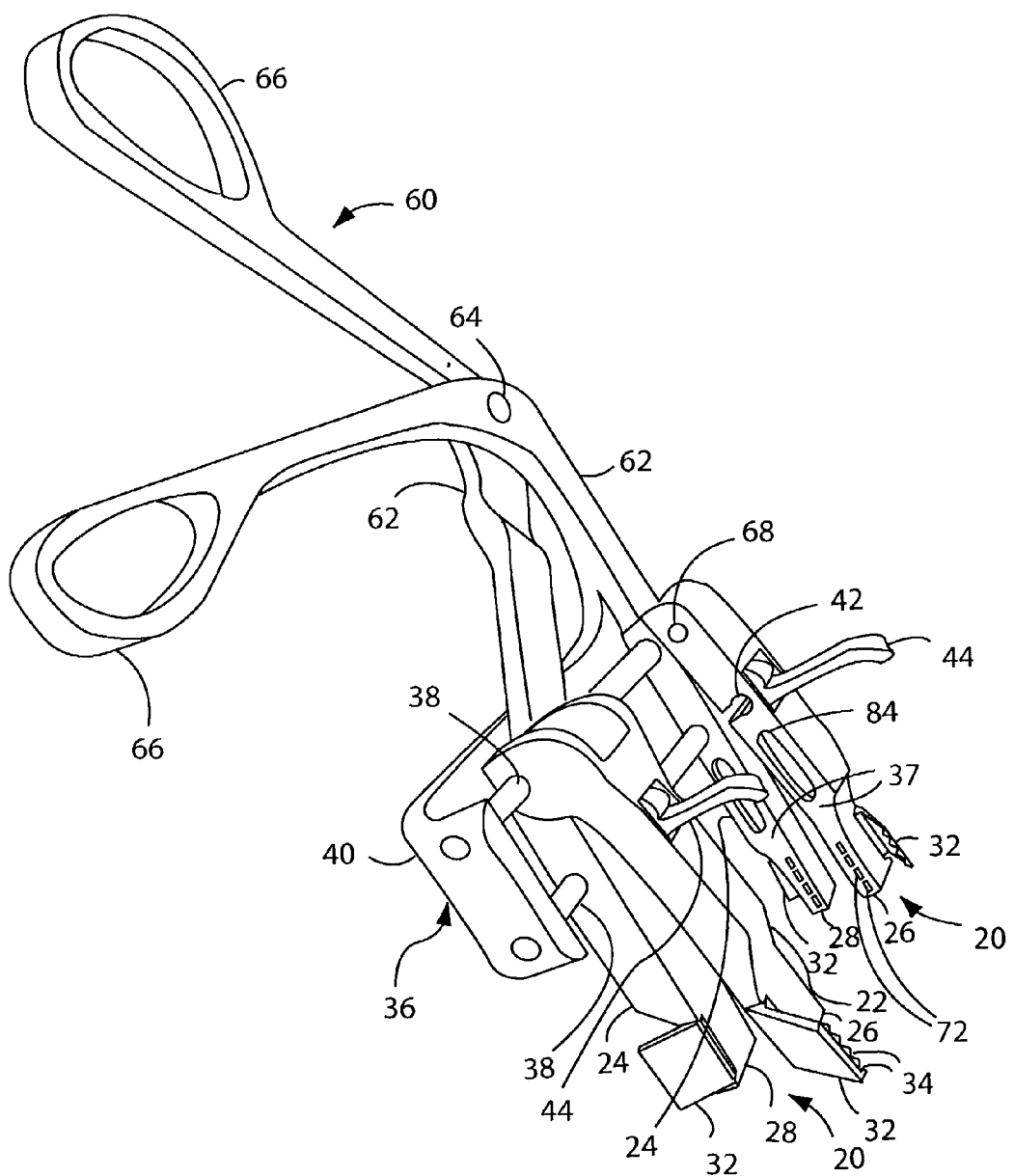
FIG. 5 is a perspective view of an anastomosis tool.

Referring to FIG. 5, an anastomosis tool 30 for performing end-to-end anastomosis is shown. The anastomosis tool 30 includes two clamps 20. Each clamp 20 includes a first arm 22 and a second arm 24. The first arm 22 has a distal end 26, and the second arm 24 has a distal end 28. The first arm 22 and the second arm 24 are both configured to rotate from an open position, in which the distal end 26 of the first arm 22 is spaced apart from the distal end 28 of the second arm 24, to a closed position, in which the distal end 26 of the first arm 22 is in proximity to the distal end 28 of the second arm 24. In the closed position, the first arm 22 and second arm 24 hold a flattened tissue structure 2, 4 between them, such that the first arm 22 is separated from the second arm 24 by the thickness of the flattened tissue structure 2, 4. Alternately, the first arm 22 and the second arm 24 are movable relative to one another in any manner as long as the first arm 22 and the second arm 24 are capable of motion between an open position and a closed position. For example, the first arm 22 and the second arm 24 may slide together to a closed position from an open position.

When in the open position, the clamp 20 is capable of receiving a tissue structure 2, 4 between the first arm 22 and the second arm 24. The tissue preparation device 12 described above is positioned on the surface of the first arm 22 that faces the second arm 24, or on the surface of the second arm 24 that faces the first arm 24. Thus, the pin 14 and the measuring feature 16 are provided on a surface of one of the arms 22, 24, and recess (not shown) corresponding to the pin 14 is provided on the corresponding surface of the other arm 22, 24, such that the arms 22, 24 can close. Where the measuring feature 16 is a pin, a recess corresponding to that pin is provided in the corresponding surface of the other arm 22, 24 as well. Thus, after the interface length 6 has been mapped onto the tissue structure 2, 4, the clamp 20 can be closed, trapping and firmly holding the tissue structure 2, 4 between the first arm 22 and the second arm 24. Advantageously, each clamp 20 holds a tissue structure 2, 4 between its arms 22, 24 without penetrating the tissue structure 2, 4 in whole or in part. Instead, each clamp 20 holds a tissue structure 2, 4 by gripping it between its arms 22, 24. In this way, the tissue structure 2, 4 is not damaged by the clamps 20, and any leakage that may result from penetration of the tissue structures 2, 4 is avoided. However, one or more of the clamps 20 may penetrate a tissue structure 2, 4 in order to hold it in place. Alternately, the tissue preparation device 12 is independent from the clamp 20. If so, the ends of the tissue structures 2, 4 are cut and flaps formed in them using an independent tissue preparation device 12, after which a user moves the ends of the tissue structures 2, 4 into clamps 20 using a forceps or other tool, or by hand.

Referring also to FIG. 1, after the interface length 6 has been mapped onto the tissue structure 2, 4 and the clamp 20 is closed, flaps 8 are cut in the end of the tissue structure 2, 4. A scissors, scalpel or other tool may be used to do so. Advantageously, two cuts are made in the walls of the tissue structure 2, 4, resulting in two flaps 8. The two cuts are made substantially one hundred and eighty degrees apart with regard to the circumference of the tissue structure, such that the flaps 8 flank the end of the lumen 10 of the tissue structure 2, 4. More cuts may be made if desired, thereby resulting in more flaps.

A tissue clip 32 is attached to each arm 22, 24 of each clamp 20. One edge of each clip 32 is attached to the surface of the corresponding arm 22, 24, and another edge of each clip 32 is free to move relative to the surface of the arm 22, 24 to allow the clip 32 to move between an open position and a closed position. Each clip 32 may include a number of teeth 34 or other gripping features at its free edge, to better grip a flap 8 of the tissue structure 2, 4 between the clip 32 and the corresponding arm 22, 24. Each clip 32 is initially in an open position in order to receive the corresponding flap 8. After the flaps 8 have been created by cutting the tissue structures 2, 4, each flap 8 is pulled relative to an arm 22, 24 of a clamp 20 such that a portion of the flap 8 extends into a space between a clip 32 and a surface of the arm 22, 24. A forceps or other tool may be used to move the flap 8. Once a portion of a flap 8 is moved into the space between a clip 32 and its corresponding arm 22, 24, the clip 32 is closed. The clip 32 includes one or more features for providing firm engagement between the free end of the clip 32 and the associated arm 22, 24 in the closed position. For example, the edge of each clip 32 that is connected to a corresponding arm 22, 24 may include a cam, lock, or other feature that engages a corresponding feature in the arm 22, 24 to hold the clip 32 closed. For example, the clips 32 may lock into place in the same or similar manner as the clamping levers 44 described below. In this way, each flap 8 is held securely against an arm 22, 24 by at least one clip 32. Advantageously, the clips 32 hold the corresponding flaps 8 under tension, such that a portion of each flap 8 is held substantially flat against a contact surface 37 of each arm 22, 24. The contact surface 37 of each arm 22, 24 is the surface that faces the corresponding arm 22, 24 of the other clamp 20. Alternately, one or more clips 32 are detachable from the clamp 20. At least one of the clips 32 may be configured to hold more than one flap 8 at a time. Such a clip 32 may be a U-shaped or C-shaped clip that extends across at least a portion of both arms 22, 24 of the clamp 20.

At least one clamp 20 is moveable relative to a jig 36, which is a component of the anastomosis tool 30. The jig 36 includes a frame 40 and two rails 38, where each rail 38 is attached at each end to the frame 40. The rails 38 are fixed to the frame 40. Alternately, the rails 38 may be moveable relative to the frame 40. The rails 38 are substantially cylindrical rods. Alternately, one or more of the rails 38 may be shaped differently. Each arm 22, 24 of each clamp 20 includes a passage defined therethrough, through which one of the rails 38 passes. The first arm 22 rotates relative to the centerline of that rail 38, thereby rotating relative to the second arm 24. The second arm 24 of each clamp 20 also includes a passage therethrough, through which a second rail 38 passes. In this way, each second arm 24 is substantially restricted to travel in a direction substantially parallel to the centerlines of the rails 38. Alternately, the arms 22, 24 are connected to the rails 38 in a different way. For example, the first arm 22 may be substantially restricted to travel in a direction substantially parallel to the centerlines of the rails 38, while the second arm 24 is free to rotate about the centerline of one of the rails 38.

Optionally, the first arm 22 of each clamp 20 includes a slot 42 defined therein. A slot 42 may be provided on one or both sides of the first arm 22. The slot 42 is positioned on the first arm 22 such that, when the clamp 20 is in a closed position, the slot 42 engages a corresponding peg (not shown) on the second arm 24. Alternately, the slot 42 engages one of the rails 38. In this way, the slot or slots 42 align the arms 22, 24. The slot 42 includes a portion having a diameter substantially the same as the corresponding peg, and a portion sized slightly narrower than the diameter of that peg, such that the slot 42 does not completely engage the peg until pressure is applied in order to force the narrow portion of the slot 42 over the diameter of the peg. Alternately, the slots 42 do not include narrow areas, and only loosely engage the peg.

Figure 6:
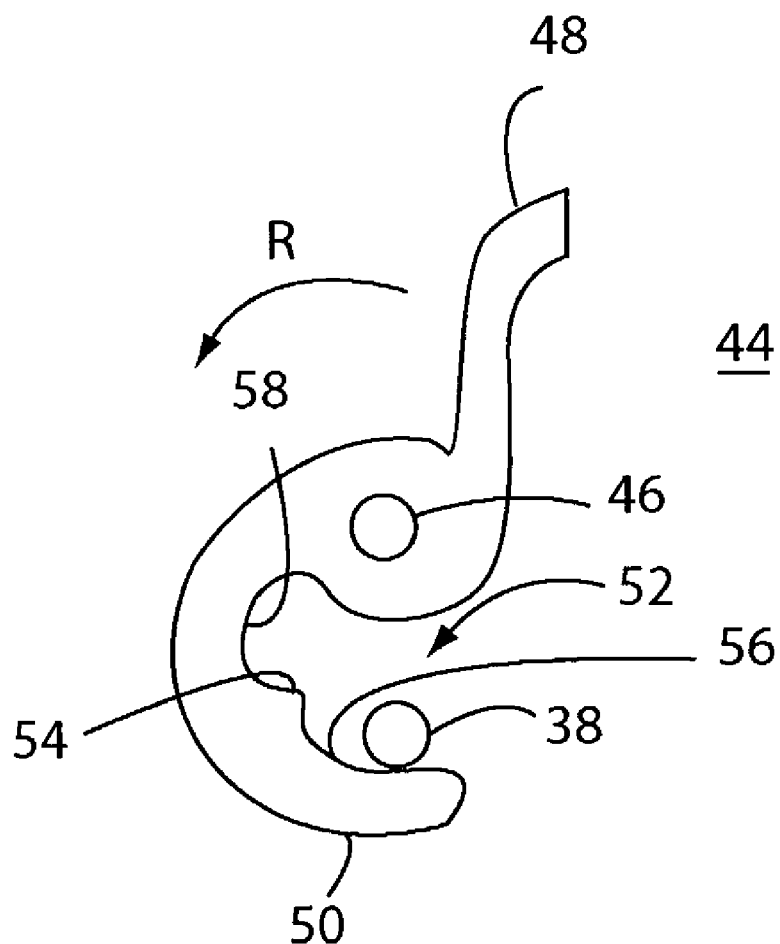
FIG. 6 is a side view of a clamping lever used as a component of the anastomosis tool.

A clamping lever 44 may also be connected to each clamp 20. Referring also to FIG. 6, the clamping lever 44 rotates around a pin 46 or other structure within the first arm 22 of each clamp 20. An interface structure 48 extends out of the first arm 22, such that a user can contact the interface structure 48 by hand or using a tool such as a forceps in order to rotate the clamping lever 44 around the pin 46. The clamping lever 44 also includes a finger 50. The finger 50 is spaced apart from the pin 46, such that a space 52 is present in the clamping lever 44 between the finger 50 and a portion of the clamping lever 44 adjacent to the pin 46. The space 52 is sized to accept a rail 38 of the jig 36. As the clamping lever 44 is rotated relative to the pin 46 in the direction R, the finger 50 moves relative to the rail 38, such that the rail 38 enters the space 52. The rail 38 may ride along an inner surface 56 of the finger 50 for at least a portion of the rotation of the clamping lever 44. The inner surface 56 may additionally have a varying radius along its length relative to the pin 46, such that the finger 50 contacts and exerts increasing force on the rail 38 during its rotation. As the clamping lever 44 continues to rotate, the rail 38 contacts a tooth 54 on the inner surface of the finger 50. Contact between the tooth 54 and the rail 38 exerts a force on the rail 38 in the direction toward the pin 46. The clamping lever 44 continues to rotate relative to the pin 46 such that the tooth 54 passes across the rail 38 and the rail 38 is received into a pocket 58 adjacent to the tooth 54. The tooth 54 prevents the clamping lever 44 from rotating back in a direction opposed to the direction R, such that the clamping lever 44 holds the rail 38 firmly. Additionally, the radius of the inner surface 56 of the finger 50 relative to the pin 46 may be less at the pocket 58 then at the end of the finger 50. The rail 38 and the pin 46 are thus pressed together. Because the pin 46 is connected to the first arm 22, the first arm 22 is pressed downward toward the rail 38, and thus pressed into the second arm 24 to ensure firm and secure engagement. The pocket 58 is shaped such that the clamp 20 may still translate along the rails 38 even after the arms 22, 24 are securely clamped together. After the pocket 58 has received the rail 38, the clamping lever 44 may be characterized as being in a locked configuration. The clamping lever 44 may be constructed such that, in the locked configuration, the interface structure 48 contacts or moves into proximity to the surface of the clamp 20.

A handle 60 is configured to move the clamps 20 closer to one another along the jig 36. After the tissue structures 2, 4 have been clamped down in the clamps 20 and the flaps 8 have been secured by the clips 34, as described above, the user may actuate the handle 60. The handle 60 may be any structure, mechanism or combination thereof that is capable of moving the clamps 20 together along the jig 36. As one example, each clamp 20 is connected to a leg 62 of the handle 60. The legs 62 are connected to one another via a pin 64 or other structure or mechanism. The legs 62 are free to pivot about the pin 64. The handle 60 may include one or more user interface features 66 such as grips. These user interface features 66 may be engaged by hand, by forceps, or by other user input. Alternately, the handle 60 may be shaped differently, or have different or additional components. Alternately, the handle 60 is not used. For example, the clamps 20 may be moved together manually, such as by hand or by forceps. As another example, the clamps 20 may be biased together, such that removal of a stop (not shown) or other structure allows the clamps 20 to move together along the jig 36 without the use of a handle 60. Additional or different structures and/or mechanisms may be used to bring the clamps 20 together along the jig 36.

Figure 7:
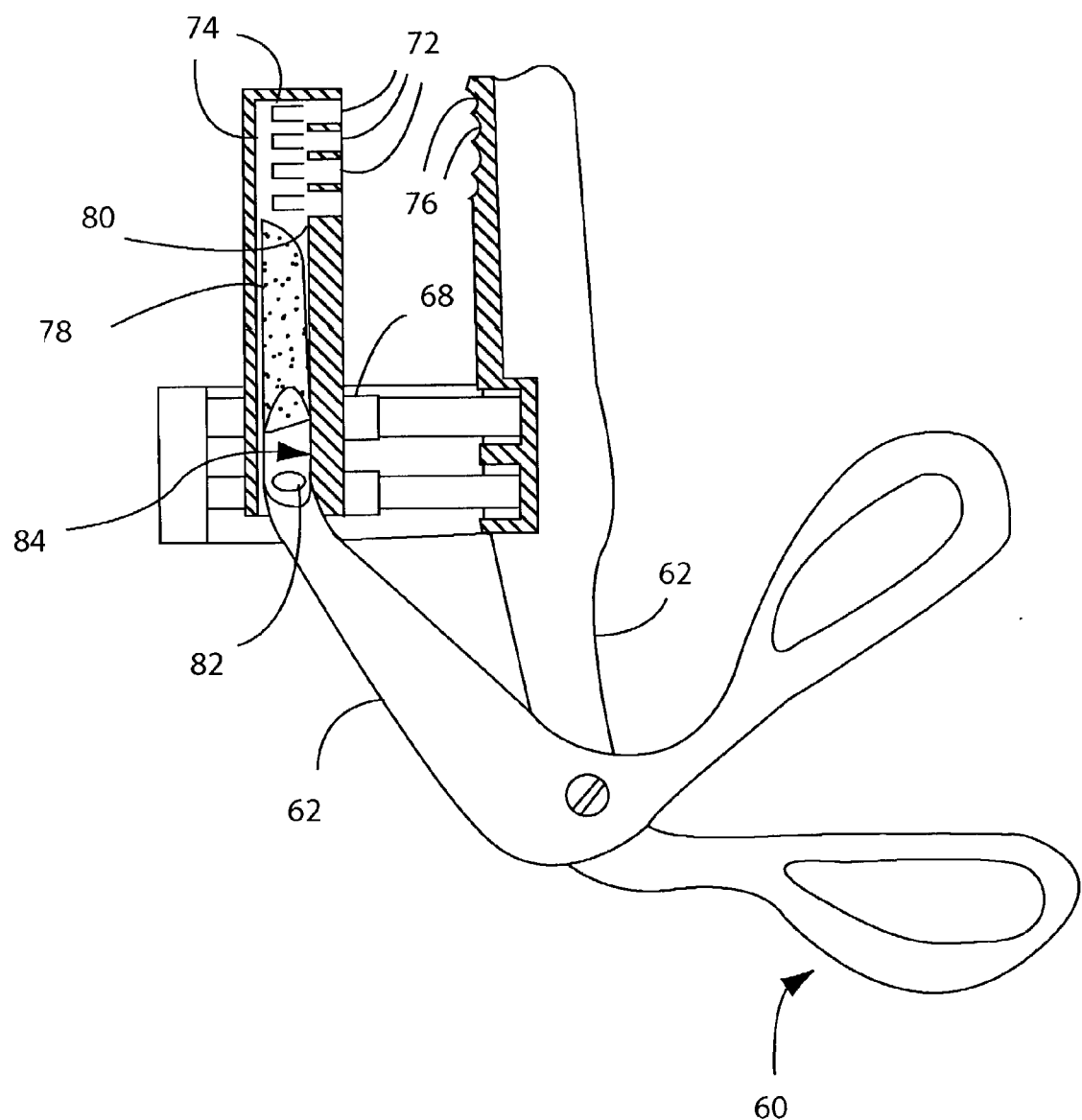
FIG. 7 is a top, partially cut-away view of the anastomosis tool of FIG. 6.

To perform anastomosis between the tissue structures 2, 4, the user actuates the handle 60, squeezing the proximal ends of the legs 62 closer together. The legs 62 begin to pivot relative to one another about the pin 64, thereby causing the distal ends of the legs 62 to move closer together. The motion of the legs 62 closer together causes the clamps 20 to move closer together along the rails 38 of the jig 36. The legs 62 are mounted to the clamps 20 in such a way as to translate the clamps 20 smoothly along the rails 38. A linkage (not shown) or a flexible segment may be used at the interface between at least one leg 62 and the corresponding clamp 20. In this way, the radius of travel of the distal end of at least one leg 62 relative to the pin 64 is converted to substantially linear motion of the corresponding clamp 20. Alternately, a cam mechanism or other mechanism may be used to produce the same substantially linear motion of the clamp 20 from the actuation of the handle 60. Referring also to FIG. 7, one leg 62 may be mounted to a clamp 20 that is fixed to the jig 36, so that it does not translate along the rails 38. Thus, that clamp 20 remains substantially stationary relative to the jig 36, and no linkage or flexible segment is needed to connected that leg 62 to the clamp 20. Alternately, that clamp 20 is not fixed to the jig 36 and the pin 64 is positioned substantially along the longitudinal centerline of that clamp 20.

Optionally, at least one alignment boss 68 is defined on or connected to at least one clamp 20. Each alignment boss 68 is a substantially cylindrical structure extending outward from the contact surface 37 of the first arm 22 of one clamp 20 toward the first arm 22 of the other clamp 20. However, one or more of the alignment bosses 68 may be shaped differently. Advantageously, two alignment bosses 68 are provided on the first arm 22 of one clamp 20. The other clamp 20 includes at least one corresponding boss receiver 70. Each boss receiver 70 is shaped to correspond to the shape of the outer surface of each alignment boss 68. Thus, where the alignment bosses 68 are substantially cylindrical, the boss receivers 70 are substantially cylindrical depressions, each having a diameter slightly larger than the outer diameter of the corresponding alignment boss 68. As each alignment boss 68 is received into the corresponding boss receiver 70, the close fit therebetween causes the two clamps 20 to align more closely. In this way, the distal ends 26, 28 of each clamp 20 are brought into close alignment with the distal ends 26, 28 of the corresponding clamp 20. Thus, the flaps 8 are registered together as they are brought into contact with one another. Alternately, at least one alignment boss 68 is positioned on the second arm 24 of at least one clamp 20 such that one of the rails 38 extends through the lumen of the alignment boss 68. Thus, the outer diameter of the alignment boss 68 is larger than the diameter of the rail 38. Alternately, rather than being tubular structures, the alignment bosses 68 are shaped differently, while still having a lumen therethrough to accept the rail 38. Alternately, each clamp 20 includes an alignment boss 68, where each alignment boss 68 is associated with a different rail 38.

In another embodiment of the tool 30, the jig 36 is not used. Rather, each clamp 20 is connected to a leg 62 of the handle 60. Alignment and registration of the clamps 20 relative to one another is provided by at least one alignment boss 68 and corresponding boss receiver 70. Thus, when the clamps 20 approach close enough to one another, each boss receiver 70 receives the corresponding alignment boss 68. As described above, the interface between each alignment boss 68 and corresponding boss receiver 70 aligns and registers the clamps 20 relative to one another. Where the jig 36 is not used, the arcuate motion of the distal end of each leg 62 of the handle 60 need not be converted to linear motion along the jig 36. In this way, construction of the tool 30 may be simplified.

Motion of the handle 60 and the clamps 20 stops when the flaps 8 contact one another, and the clamps 20 thus cannot move substantially closer to one another. This configuration of the anastomosis tool 30 may be referred to as the deployment position. In the deployment position, the contact surfaces 37 may be spaced apart from each other a small distance, due to the thickness of each flap 8. Alternately, the contact surface 37 of one clamp 20 may contact the contact surface 37 of the other clamp 20. The clamps 20 are not affirmatively locked together; rather, continued actuation of the handle 60 holds the clamps 20 together after the flaps 8 contact one another. Alternately, a locking mechanism (not shown) holds the clamps 20 together after the flaps 8 are brought into contact with one another. The locking mechanism may be a component of one or more clamps 20, of the jig 36, or may be a separate component used to hold the clamps 20 together.

In the deployment position, the flaps 8 are in a mating configuration. That is, each flap 8 on the first tissue structure 2 is pressed against a corresponding flap 8 on the corresponding tissue structure 4. Where the tissue structures 2, 4 are blood vessels, the mating surface of each flap 8 is a portion of the intimal lining of that blood vessel, and the flaps 8 are pressed together such that their intimal surfaces contact one another. After the flaps 8 are brought together, they are connected to one another. At least one clamp 20 includes one or more connector deployers 72. The connector deployers 72 are structures or mechanisms for deploying connectors 74 into the flaps 8 to connect them together. The connectors 74 are staples. Alternately, the connectors 74 are any other connectors, fasteners, structures or mechanisms useful for connecting the flaps 8 of the first tissue structure 2 to the flaps 8 of the second tissue structure 4. One example of a connector deployer 72 is an opening in a clamp 20, with a connector 74 held adjacent to that opening, such as by a friction fit. Other mechanisms may be used as connector deployers 72. A connector receiver 76 may be provided opposite one or more of the connector deployers 72 on the other clamp 20. For example, if the connectors 74 are staples, then the connector receivers 76 are staple-forming surfaces configured to bend the staples into a configuration in which they hold mating flaps 8 together. The connector receivers 76 may be shaped differently, and may be omitted altogether, depending on the characteristics of the connector 74 that is utilized. Advantageously, connector deployers 72 are provided in a single clamp 20, in order to simplify their actuation. However, connector deployers 72 may be placed in more than one clamp 20, if desired. Referring also to FIGS. 1 and 5, connector deployers 72 are located on each arm 22, 24 of at least one clamp 20. By providing connector deployers 72 on each arm 22, 24, connectors 74 can be deployed around the lumen 10 of each tissue structure 2, 4. That is, connectors 74 can be deployed through the flaps 8 of the tissue structures 2, 4 such that they are placed substantially evenly around the circumference of the lumen 10 of each tissue structures 2, 4. Alternately, the connector deployers 72 can be positioned differently within the arms 22, 24 of at least one clamp, as long as such a position allows the flaps 8 to be connected together securely and substantially without leakage. Alternately, the connector deployers 72 do not deploy physical connectors, but rather apply energy or otherwise manipulate the flaps 8 to connect them. Such connector deployers 72 may be tissue-welding electrodes, waveguides, or mechanisms for delivering adhesive.

Referring to FIG. 7, at least one actuator 78 is connected to at least one leg 62 of the handle 60. Each actuator 78 is constrained to move within a channel 80 within each arm 22, 24 in which connector deployers 72 are placed. After the flaps 8 of the tissue structures 2, 4 have been brought together, at least one leg 62 continues in its motion, or otherwise causes the actuator 78 to move. The actuator 78 is a piece of material that fits within the channel 80, and which is shaped at its distal end in such a way as, when it is urged distally, to cause the connector deployers 72 to deploy connectors 74. As one example, the distal end of the actuator 78 is curved or angled relative to connectors 74 that extend at least partially into the channel 80 before they are deployed. In this example, the connector deployers 72 are simply passages between the channel 80 and the contact surface 37 of the clamp 20. As the leg 62 continues to move as the handle 60 is compressed, the leg 62 urges each actuator 78 distally along the channel 80. The distal end of each actuator 78 engages each connector 74 in the arm 22, 24, serially pushing each connector 74 out of the channel through the corresponding passage of the connector deployer 72. As the distal tip of the actuator 78 passes by each connector deployer 72, the full width of the actuator 78 passes through the channel 80 and presses against the connector 74, forcing it out of the connector deployer 72. Where the connectors 74 are staples, this force presses the connectors 74 against corresponding connector receivers 76, causing them to bend and thus connect the mated flaps 8 together. Other actuators 78 may be used instead. Further, where connector deployers 72 are provided in more than one clamp 20, an actuator 78 is provided in each clamp 20. The actuators 78 need not have the same configuration or construction in each clamp 20.

As described above, at least one leg 62 may includes a linkage or flexible portion to allow the end of the leg 62 to rotate through an arc relative to a pin 64 while at the same time translating the connected clamp 20 in a linear direction. As seen in FIG. 7, such a linkage may include a pin 82 connected to the leg 62, where that pin 82 is moveable through a slot 84 in the clamp 20. When the clamps 20 are pressed together, the leg 62 continues to move, continuing to urge the pin 82 along the slot 84, where that pin 82 engages the actuator 78 and causes the connectors 74 to deploy. The linkage or flexible element connecting the leg 62 to the clamp 20 may be configured to allow the pin 82 to move along the slot 84. Alternately, an additional linkage or element may be provided to allow the pin 82 to move along the slot 84 as the handle 60 continues to be compressed or otherwise actuated. Thus, a continued smooth motion of the handle 60 brings the flaps 8 of the tissue structures 2, 4 together and deploys the connectors 74 into them.

Figure 8:
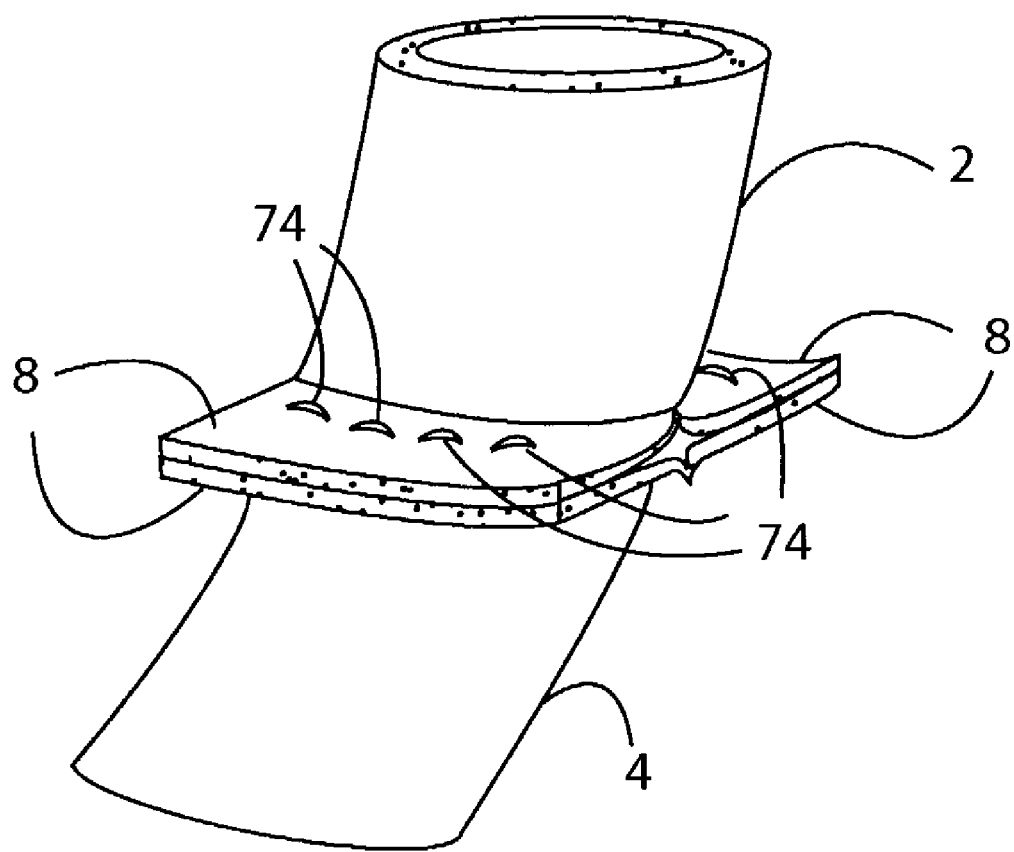
FIG. 8 is a perspective view of a completed end-to-end anastomosis.

After the connectors 74 have been deployed, the tissue structures 2, 4 are connected together, as shown in FIG. 8. The flaps 8 of the first tissue structure 2 have been connected to the flaps 8 of the second tissue structure 4 with at least one connector 74. As shown in FIG. 8, a number of connectors 74 have each penetrated one flap 8 of the first tissue structure 2 and an abutting flap 8 of the second tissue structure 4. Advantageously, the connectors 74 are spaced apart from one another a distance comparable to the distance between stitches in a sutured anastomosis. The flaps 8 are then freed from the clips 32. A tissue knife (not shown) may be used in conjunction with each clip 32 to free the associated flap 8, as well as to cut excess flap tissue away from the anastomosis. Each tissue knife is a cutting structure or mechanism that does not engage the flaps 8 until the connectors 74 have been deployed. As each actuator 78 is urged distally, it engages the corresponding tissue knife, such that the actuator 78 causes the tissue knife to cut through the flaps 8, cutting the flaps 8 completely free of the clips 32 after the connectors 74 have all been deployed. As one example, a slot (not shown) on the contact surface 37 of each clamp 20 is located under each flap 8, and a tissue knife is deployed out of and along each such slot in order to cut the corresponding flap 8. Alternately, a structure or mechanism other than the actuator 78 may be used to activate the tissue knives. Alternately, the tissue knives are not used, and a forceps or other tool is used to lift the clips 32 from their closed positions and free the flaps 8.

Referring also to FIG. 5, a passage 86 optionally may be defined through the contact surface 37 of each arm 22, 24. A finger (not shown) extends through adjacent pairs of passages 86. The finger transmits the motion of the actuator 78 or other mechanism from one arm 22, 24 to the adjacent arm 22, 24 in the other clamp 20 in order to actuate the tissue knives in that clamp 20. That is, motion of each actuator 78 is transmitted to a corresponding finger, which moves through the corresponding passage 86 in one arm 22, 24 to actuate the corresponding tissue knife in the other arm 22, 24. Alternately, the passages 86 are not provided, and the tissue knives in the other clamp 20 are actuated with a mechanism within that clamp 20. The clamping levers 48 are then rotated out of their locked configuration, and the arms 22, 24 of each clamp 20 separate to allow the connected tissue structures 2, 4 to be freed easily from the tool 30.

Although the tool above has been described in the context of microvascular anastomosis, the tool also may be used to perform end-to-end anastomosis between hollow tissue structures other than small-diameter blood vessels, such as larger blood vessels, intestinal segments, ducts such as the bile duct, and other hollow tissue structures. The tool may also be used to perform end-to-end connections between solid tissue structures such as muscles, tendons and nerves, particularly solid tissue structures having a small cross-section. Flaps can be created at the end of such solid structures as described above, and those solid structures can be connected end-to-end by those flaps in the same manner as described above. Additional or different fasteners may be used to connect such flaps to ensure that the solid structures are firmly connected to one another.

Figure 9:
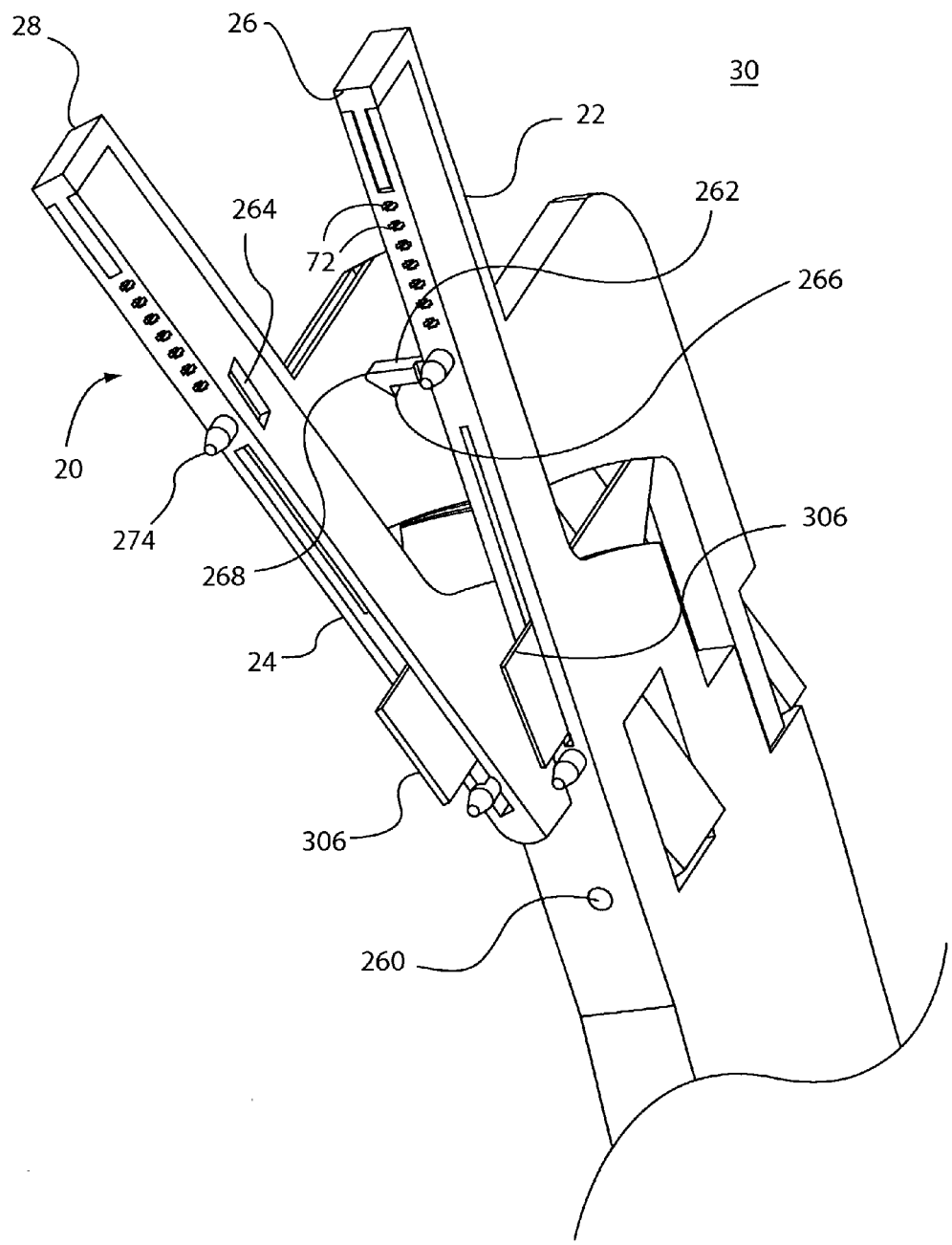
FIG. 9 is a perspective view of a portion of the distal end of the anastomosis tool, showing a clamp having its two arms in an open position.

Referring to FIGS. 9–14, another embodiment of an anastomosis tool 30 is shown. As in the embodiment described above, the anastomosis tool 30 includes two clamps 20, where each clamp 20 includes a first arm 22 and a second arm 24. Referring particularly to FIG. 9, a single clamp 20 of the anastomosis tool is shown. The first arm 22 has a distal end 26, and the second arm 24 has a distal end 28. The first arm 22 and the second arm 24 are both configured to rotate from an open position, in which the distal end 26 of the first arm 22 is spaced apart from the distal end 28 of the second arm 24, to a closed position, in which the distal end 26 of the first arm 22 is closer to the distal end 28 of the second arm 24. At least one of the first arm 22 and the second arm 24 rotate about a pin 260 to move between the open and the closed position. One of the arms 22, 24 may be fixed to the pin 260, while the other arm 22, 24 is free to rotate relative to the pin 260. A different structure or mechanism may be provided to move the arms 22, 24 between the open and the closed position. Further, the first arm 22 and the second arm 24 may be movable relative to one another in any other manner as long as the first arm 22 and the second arm 24 are capable of motion between an open position and a closed position.

As shown in FIG. 9, the clamp 20 is in the open position, and is capable of receiving a tissue structure 2, 4 as shown in FIGS. 2–4 between the first arm 22 and the second arm 24. The tissue structure 2, 4 is not shown in FIG. 9 for clarity. Referring to FIGS. 2–4, the ends of the tissue structures 2, 4 are cut and flaps formed in them using the independent tissue preparation device 12 described above, after which a user moves the ends of the tissue structures 2, 4 into clamps 20 using a forceps or other tool, or by hand. Alternately, the tissue preparation device 12 may be positioned on the surface of the first arm 22 that faces the second arm 24, or on the surface of the second arm 24 that faces the first arm 24, as described above. A tissue clip may be attached to each arm 22, 24, as described above. However, the tissue clips are not shown in FIGS. 9–14 for clarity in illustrating the anastomosis tool 30. Each flap 8 of a tissue structure 2, 4 may be held securely by at least one clip 32.

A catch 262 extends from the first arm 22 toward the second arm 24. A corresponding aperture 264 is formed into the second arm 24. Alternately, the catch 262 extends from the second arm 24 toward the first arm 22, and a corresponding aperture 264 is formed into the first arm 22. Alternately, multiple catches 262 and multiple apertures 264 are used. The catch 262 and the corresponding aperture 264 are positioned relative to one another such that the catch 262 enters the aperture 264 when the clamp 20 is closed. The catch 262 includes a tooth 266 extending proximally, and has a substantially curved end 268. Alternately, the tooth 266 extends in a different direction, or more than one tooth 266 is provided. Alternately, the end 268 of the catch 262 is not curved, and is instead shaped differently.

Figure 10:
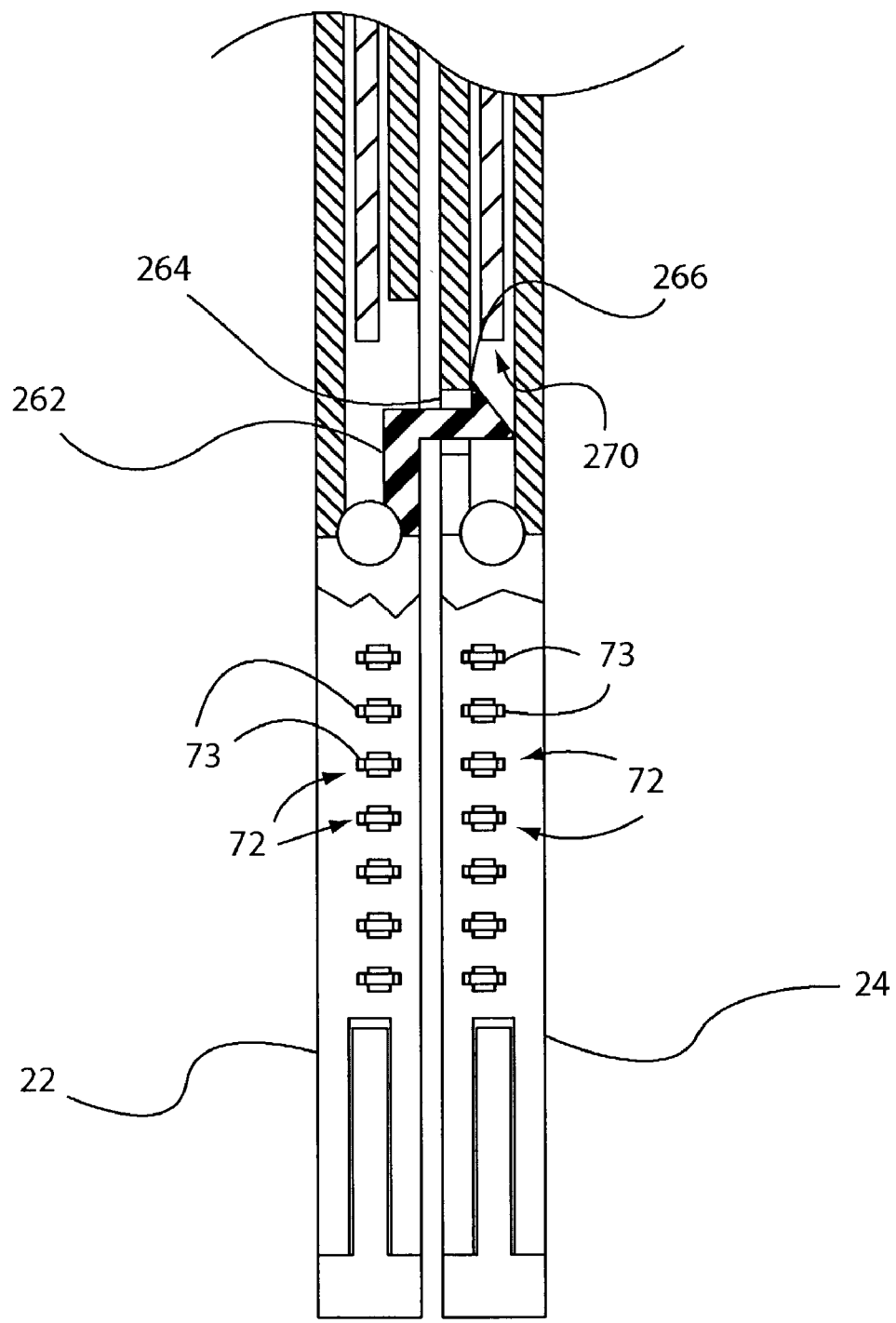
FIG. 10 is a plan view of the two arms of the clamp of FIG. 9 in a clamped position, cut away to show a partial cross-section of the clamp.

Referring also to FIG. 10, as the arms 26, 28 are brought closer together, the end 268 of the catch 262 begins to enter the aperture 264 in the second arm 24. The catch 262 may be positioned such that at least a portion of the rounded end 268 contacts an edge of the aperture 264. This contact causes the end 268 of the catch 262 to deflect gradually in a distal direction as the arms 26, 28 are brought closer together. Alternately, the end of the catch 262 may deflect gradually in a proximal direction, depending on the relative positions of the catch 262 and the corresponding aperture 264. The aperture 264 may open into a second channel 270 within the second arm 24. The catch 262 continues to deflect distally until the tooth 266 of the catch 262 passes through the aperture 264, at which time the end 268 of the catch 262 moves distally. That is, the catch 262 begins in a neutral position, and deflection of the catch 262 away from that neutral position results in a force that acts to move the catch toward the first position. The tooth 266 extends proximal to the proximal edge of the aperture 264, thereby preventing the arms 26, 28 from separating after the clamp 20 has closed. In this way, the tissue structure (not shown) is held securely between the arms 26, 28, and the first arm 22 is separated from the second arm 24 by the thickness of the tissue structure. Alternately, the catch 262 extends from the second arm 24 toward the first arm 22, and the aperture 264 and second channel 270 are provided in the first arm 22.

Figure 11:
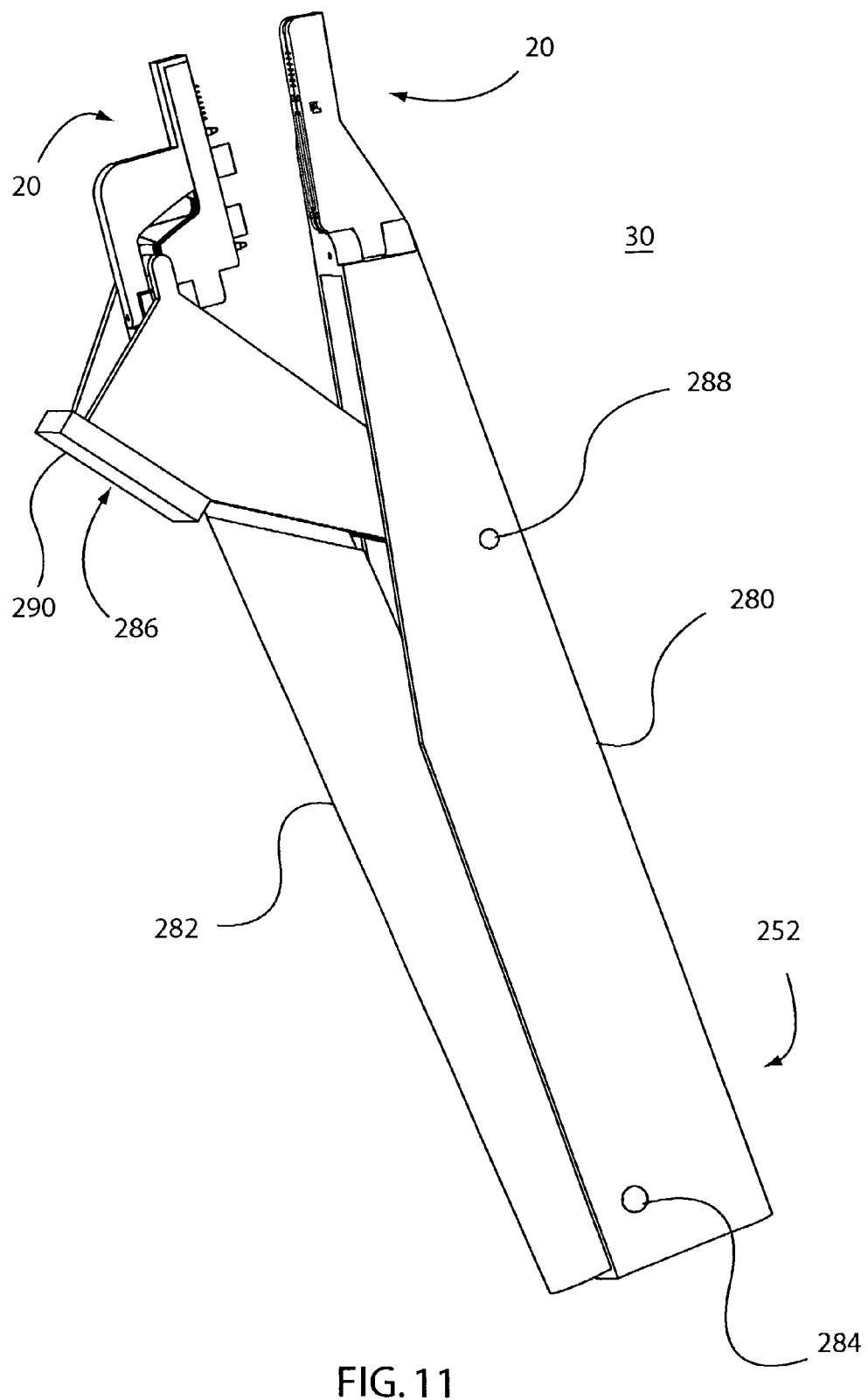
FIG. 11 is a perspective view of the anastomosis tool in a first position.

Referring also to FIG. 11, the clamps 20 are brought together by actuating the handle 252 of the anastomosis tool 30. The handle 252 is configured to allow one-handed actuation. However, the handle 252 may be configured to allow two-handed actuation, or to allow powered, robotic, automated, or other actuation. The handle 252 includes a first member 280 connected to one clamp 20, and a second member 282 connected to the other clamp 20. The first member 280 and the second member 282 are moveable toward one another. As an example, the first member 280 and the second member 282 pivot relative to one another about a pin 284. The first member 280 or the second member 282 may be fixed to the pin 284, where the other member is free to pivot about the pin 284. Further, the first member 280 may have an open cross section, such as a substantially U-shaped cross-section, into which the second member 282 is at least partly received when the members 280, 282 are moved closer to one another. Alternately, the second member 282 may have an open cross section, such as a substantially U-shaped cross section, into which the first member 280 is at least partly received when the members 280, 282 are moved closer to one another.

Figure 14:
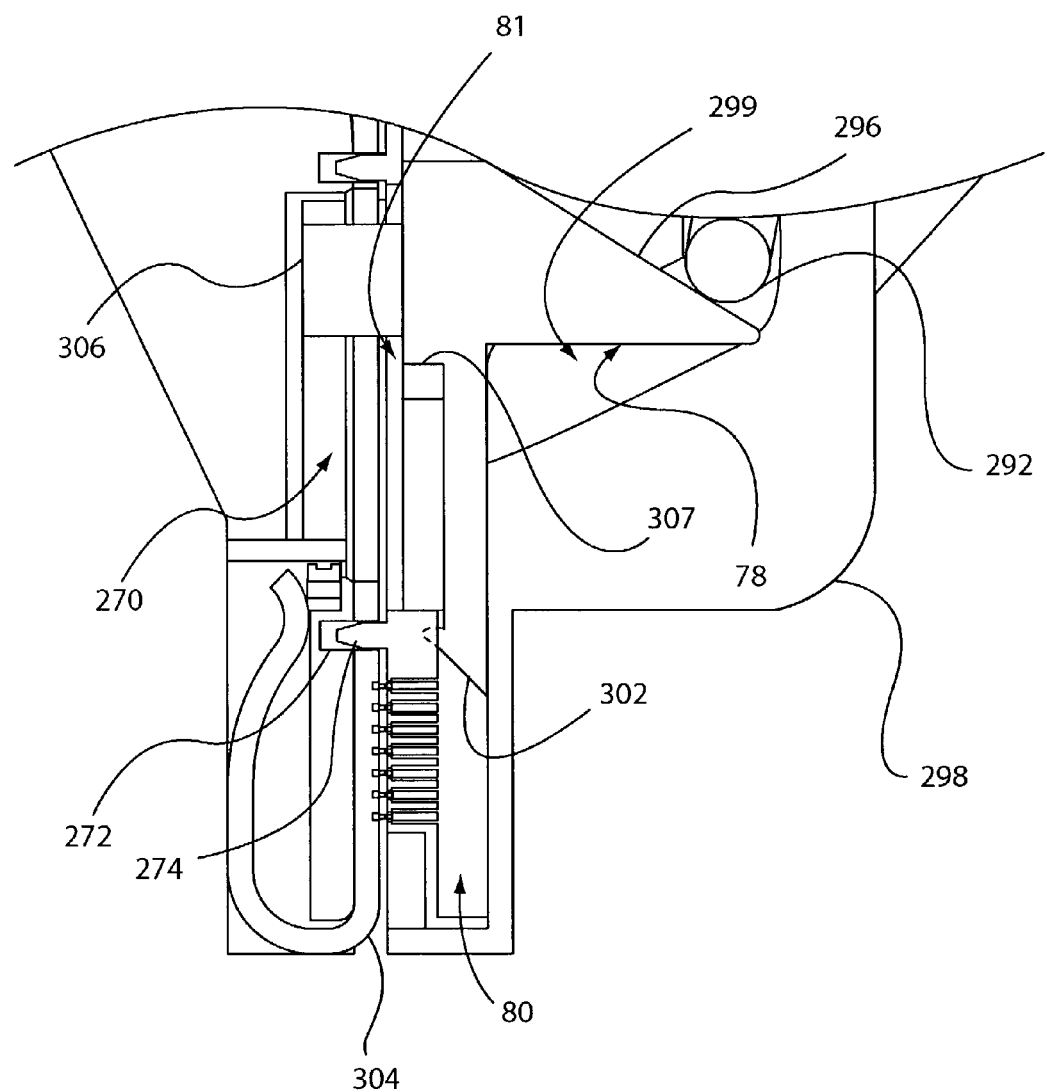
FIG. 14 is a side cutaway view of the anastomosis tool in the position of FIG. 1A.

A trigger 286 is connected to the first member 280. As an example, the trigger 286 and the first member 280 pivot relative to one another about a pin 288. Alternately, the trigger 286 is connected to the second member 282. The trigger 286 or the first member 280 may be fixed to the pin 288, while the other is free to pivot about the pin 288. However, both the trigger 286 and the first member 280 may be free to pivot about the pin 288. The trigger 286 has a substantially open cross-section, such as a U-shaped cross section. Thus, the trigger 286 defines an open volume within it. The second member 282 is positioned at least partly within the open volume within the trigger 286, and is able to move relative to the first member 280 while within the open volume of the trigger 286. The trigger 286 is itself positioned at least partly within the open volume of the first member 280. Alternately, the first member 280, second member 282 and trigger 286 may be shaped differently, and/or positioned differently relative to one another. A biasing element (not shown) may be positioned between the trigger 286 and the second member 282. The biasing element biases the trigger 286 away from the second member 282. The trigger 286 may include a pad 290 formed into or attached to it, configured to be pressed by a user's thumb or finger. Alternately, the pad 290 may be omitted, or may be positioned to be engaged differently by the user. Referring also to FIG. 14, the trigger 286 includes a crossbar 292. The crossbar 292 extends across the open volume within the trigger 286, and may be positioned near the distal end of the trigger 286. The crossbar 292 is substantially cylindrical in shape, but may be shaped differently, if desired.

Referring to FIG. 9, each clamp 20 of the anastomosis tool 30 is initially open. A tissue structure 2, 4 is received into each open clamp 20. Referring as well to FIG. 10, the clamp 20 is then closed. As described above, the catch 262 engages the aperture 264 when the clamp 20 is closed, thereby holding the clamp 20 shut. The tissue structure 2, 4 within each clamp 20 thus is held securely therein. Flaps may be cut in each tissue structure 2, 4 before or after they are clamped, as described above.

Figure 12:
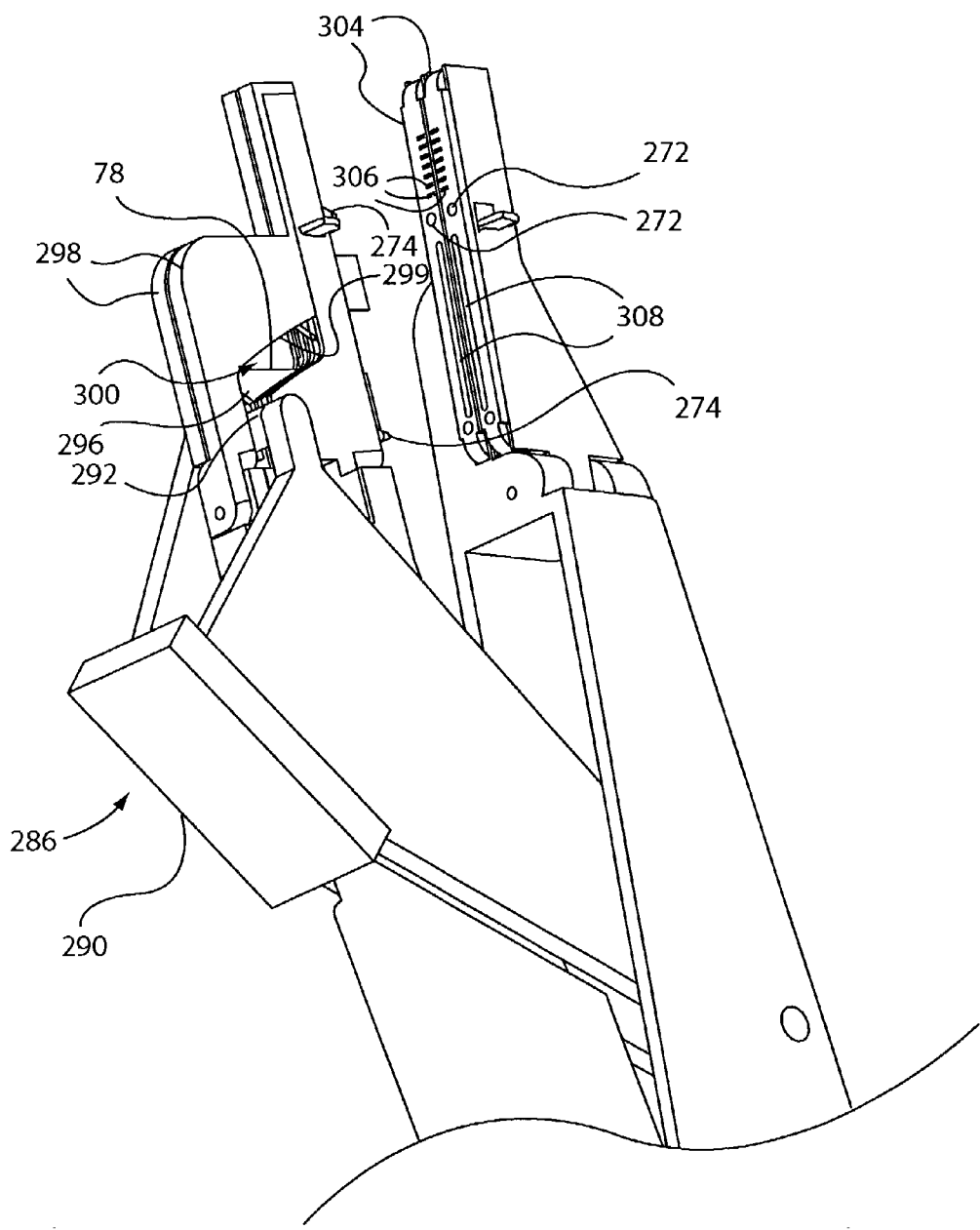
FIG. 12 is a perspective cutaway view of the distal end of the anastomosis tool in the position of FIG. 11.
Figure 13:
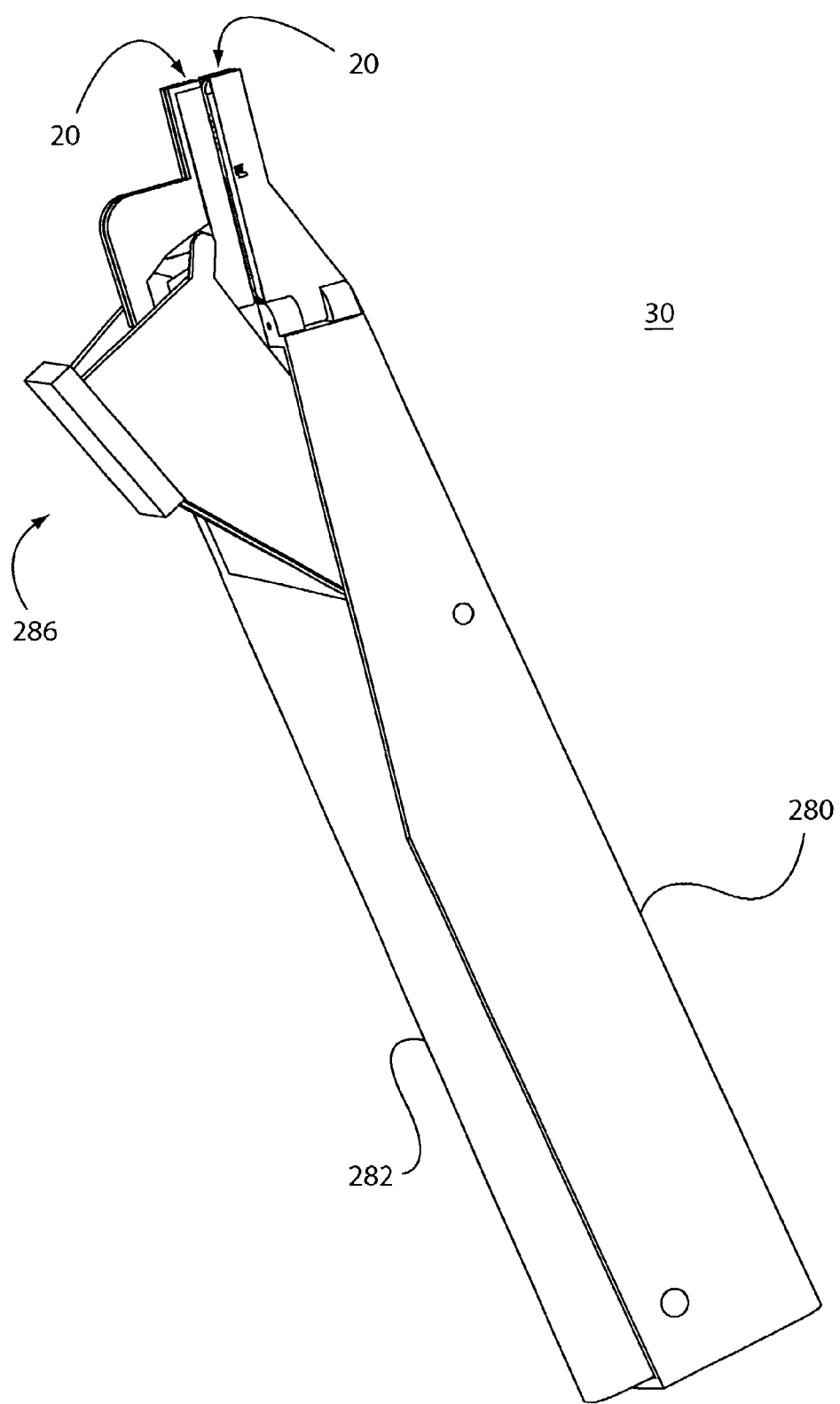
FIG. 13 is a perspective view of the anastomosis tool in a third position.

Referring to FIGS. 1 and 11, after the clamps 20 are closed, the anastomosis tool 30 is in a first position. Referring also to FIG. 12, the first member 280 and the second member 282 are then moved closer to one another, for example by squeezing them together with one hand. Referring also to FIG. 12, at least the first arm 22 of at least one clamp 20 optionally includes at least one opening 272 defined therein. Additionally, a corresponding peg or pegs 274 are included on the second arm 24 of at least one clamp 20. The opening or openings 272 are positioned on the first arm 22 such that, when the clamps 20 are brought together, the peg or pegs 274 engage the corresponding openings 272. As the clamps 20 are brought together, the peg or pegs 274 on the first arm 22 enter the corresponding opening or openings 272 on the second arm 24. The entry of one or more pegs 274 into corresponding openings 272 acts to align the arms 22, 24 properly relative to one another and to substantially prevent lateral motion of the arms 22, 24 relative to one another when the clamp 20 is closed. Each opening 272 may have a diameter substantially the same as or larger than the diameter of the corresponding peg 274 along part of its depth, and a diameter sized slightly narrower than the diameter of that peg 274 along another portion of its depth. As a result, the peg 274 does not completely engage the opening 272 until pressure is applied in order to force at least a portion of the peg 274 into the narrow segment of the opening 272. Alternately, each opening 272 loosely engages the corresponding peg 274. Alternately, the peg or pegs 274 may be provided on the first arm 22, and the corresponding opening or openings 272 are provided on the second arm 24. Alternately, each clamp 20 may include one or more pegs 274 on each arm 22, 24 and corresponding openings 272 on each arm 22, 24 as well.

Figure 11A:
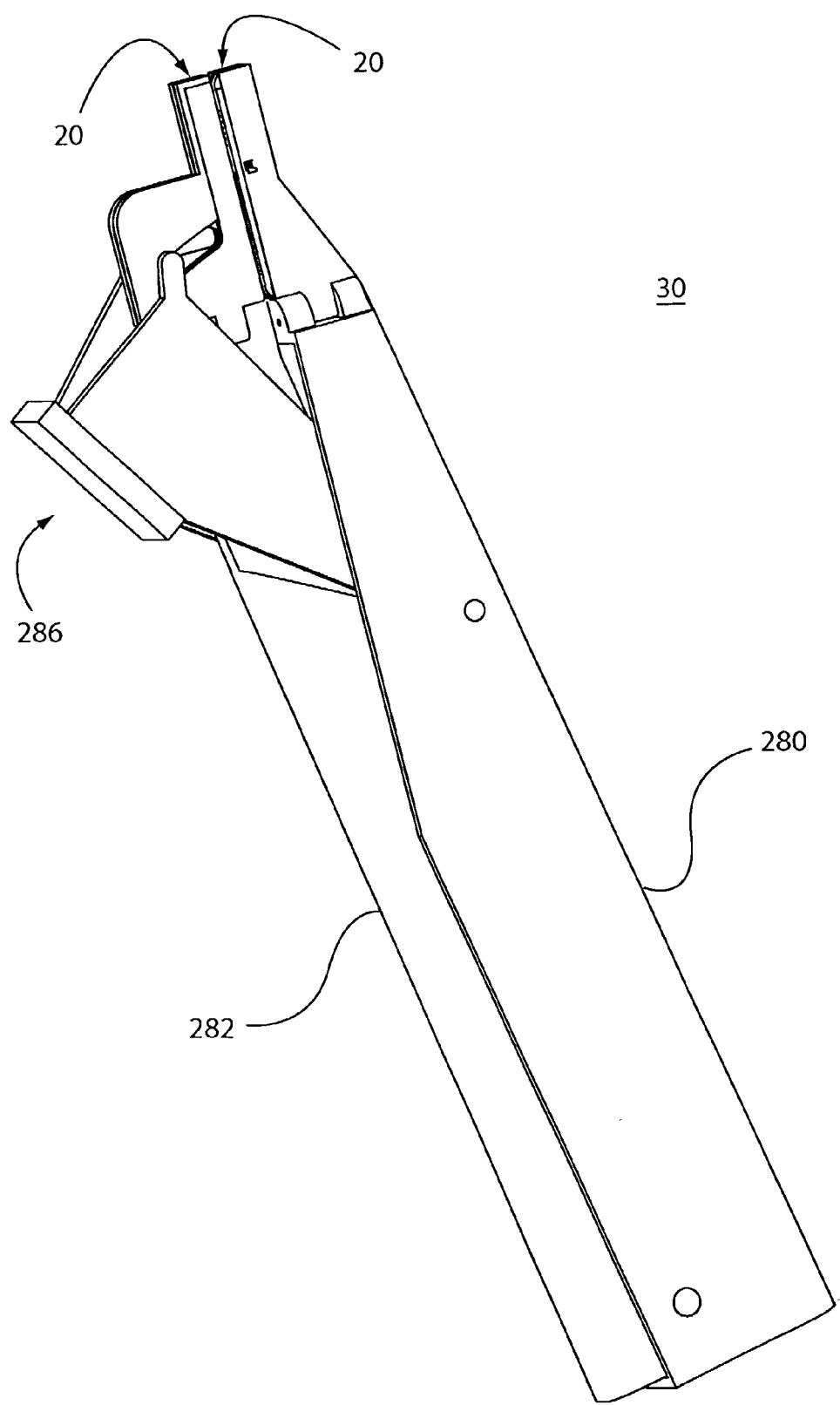
FIG. 11A is a perspective view of the anastomosis tool in a second position.

Referring to FIG. 11A, the clamps 20 continue to move closer to one another until the flaps 8 of one tissue structure 2 are brought into contact with the flaps 8 of the other tissue structure 4. The first member 280 and the second member 282 are configured such that they cannot substantially move any closer relative to one another after the flaps 8 of the tissue structures 2, 4 are pressed into contact with one another, at which point the anastomosis tool 30 is in a second position. After the first member 280 and second member 282 have been moved to the second position, the first member 280 and second member 282 may be locked or otherwise restrained relative to one another. Any suitable mechanism or structure may be used to lock the members 280, 282 together. For example, a catch and aperture (not shown) may be used to hold the members 280, 282 together, where the catch and aperture are analogous to the catch 262 and aperture 264 used to hold the arms 22, 24 of each clamp 20 together. As another example, one or more pegs 274 may include a tooth (not shown) configured to engage a ledge (not shown) in the corresponding opening 272 after the peg or pegs 274 have been received therein. As another example, the continued application of force by the user on the first member 280 and the second member 282 holds the members together. As another example, where a biasing element is provided between the trigger 286 and the second member 282, the biasing element continues to press the second member 282 away from the trigger 286 as the trigger 286 is depressed, thereby pressing the second member 282 against the first member 280.

Referring also to FIGS. 12 and 14, the user then actuates the trigger 286, such as by depressing the pad 290. The trigger 286 begins to rotate about the pin 288, causing the crossbar 292 to rotate about the pin 288 as well. Thus, the crossbar 292 moves distally, as well as in a direction toward the first member 280. The longitudinal centerline of the crossbar 292 may be substantially parallel to both of these components of its rotational motion.

As the crossbar 292 moves, it engages at least one actuator 78. Each actuator 78 is configured to translate at least partially within a channel 80 that is defined within an arm 22, 24 of the clamp 20. As one example, two actuators 78 are used, where each actuator 78 is configured to translate relative to a channel 80 defined in the first arm 22 of each clamp 20. As another example, two actuators 78 are used, where each actuator 78 is configured to translate relative to a channel 80 defined in the second arm 24 of each clamp 20. Each actuator 78 includes an engagement member 296 that may be positioned at or near its proximal end. However, the engagement member 296 may be positioned at a different location on the actuator 78. As the crossbar 292 moves, it engages the actuator 78 by contacting the engagement member 296. Alternately, the crossbar 292 engages a different or an additional portion of the actuator 78. The engagement member 296 may be angled relative to the longitudinal centerline of the clamp 20. The particular angle is selected such that the rotary motion of the crossbar 292 is converted at least partially into linear motion of the actuator 78 in the distal direction as a result of contact between the crossbar 292 and the engagement member 296. Further, the actuator 78 may be at least partially restrained within the channel 80 such that motion of the actuator 78 in any direction other than translation in a distal or proximal direction is substantially constrained.

A guard 298 may be connected to at least one arm 22, 24 in which an actuator 78 is provided. The guard 298 extends away from the arm 22, 24 to which it is connected. Each guard 298 may be configured to allow motion of the actuator 78 relative to it. For example, each guard 298 may be shaped to include a recess 299 into which at least a portion of the actuator 78 is received as the actuator 78 translates distally, where that recess 299 prevents interference between the guard 298 and the engagement member 296. Further, the guard 298 may be configured to prevent the user or external objects from inadvertently moving the actuator 78 due to accidental contact with it. Each guard 298 is also shaped to allow motion of the crossbar 292 relative to the engagement member 296. That is, an open space 300 is defined between at least a portion of the guard 298 and at least a portion of the arm 22, 24 to which it is attached in order to allow for motion of the crossbar 292 into that open space 300. Alternately, one or more of the guards 298 may be configured differently.

Figure 18:
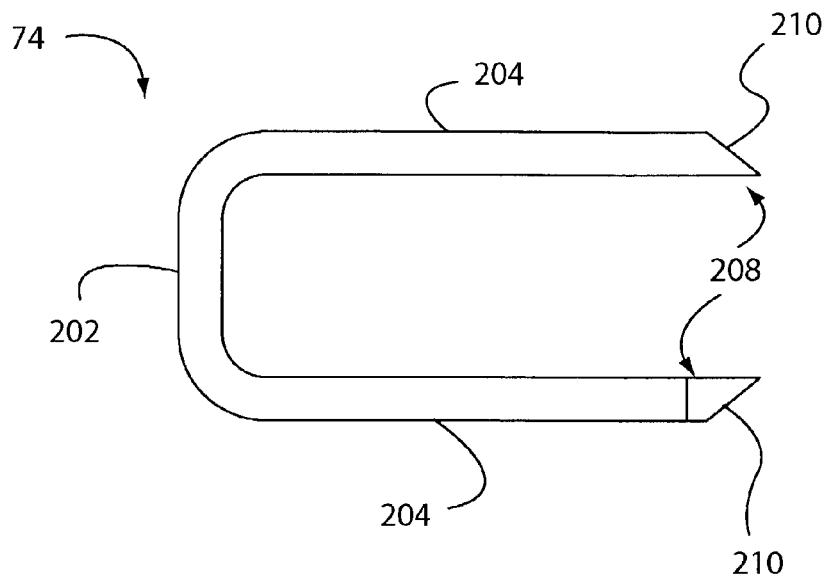
FIG. 18 is a top view of an anastomosis connector.
Figure 19:
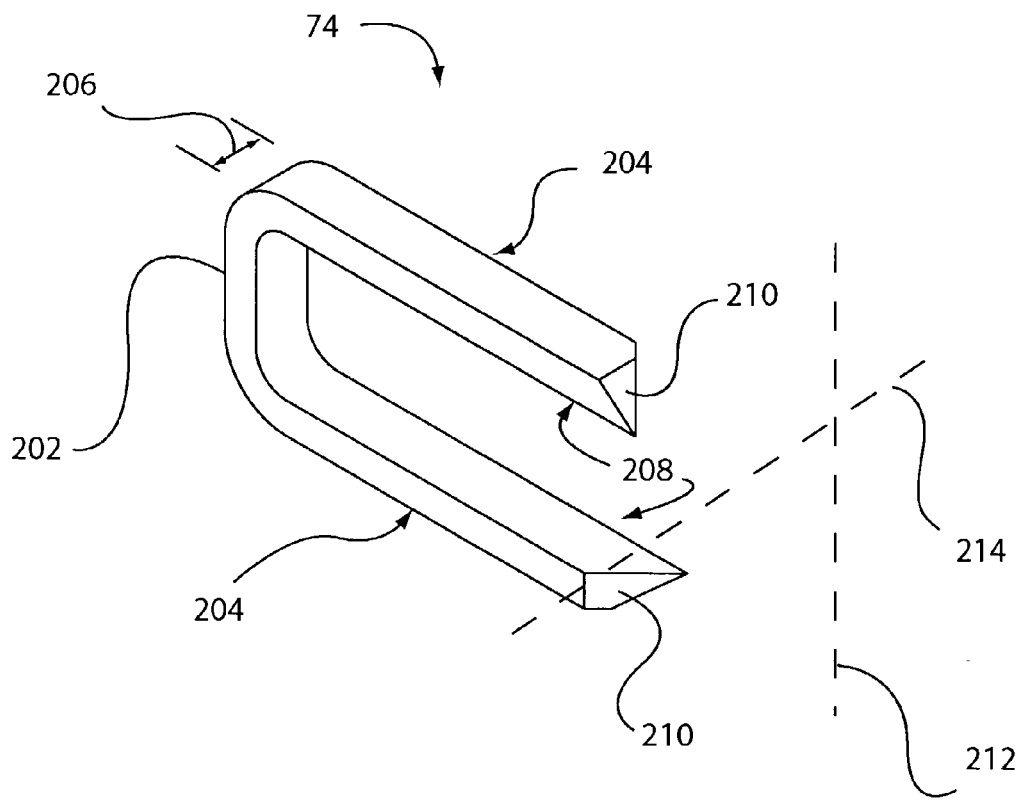
FIG. 19 is a perspective view of an anastomosis connector.

As described above, at least one clamp 20 includes one or more connector deployers 72 for deploying connectors 74 into the flaps 8 to connect them together. Referring as well to FIGS. 18–19, an exemplary connector 74 for use with the anastomosis tool 30 is shown. The connector 74 is a staple that includes a base 202 and two legs 204, each leg 204 extending from an end of the base 202. The two legs 204 are substantially parallel to one another, and extend in substantially the same direction from the base 202. However, the legs 204 may be positioned relative to one another in a non-parallel configuration. Further, more than two legs 204 may extend from the base 202. The intersection between the base 202 and each leg 204 is curved, such that the connector 74 is substantially U-shaped. However, the intersection between the base 202 and one or both legs 204 may be a substantially right angle, or another configuration. The base 202 and the legs 204 are substantially the same thickness, such that the connector 74 has a substantially constant thickness 206 at all locations. However, the thickness 206 of the connector 74 may vary at different locations. Each leg 204 has a tip 208 at an end opposite to the connection between the leg 204 and the base 202. Each tip 208 is beveled, where the bevel defines a bevel surface 210. Each bevel surface 210 is substantially planar. The bevel surfaces 210 are oriented differently from one another, such that the bevel surfaces 210 are neither co-planar with one another nor parallel to one another. However, the bevel surfaces 210 may be oriented differently, if desired. For example, the bevel surfaces 210 may be substantially parallel to one another, or substantially co-planar with each other. Alternately, the connectors 74 may be staples or any other connectors, fasteners, structures or mechanisms useful for connecting the flaps 8 of the first tissue structure 2 to the flaps 8 of the second tissue structure 4. Alternately, one or more of the tips 208 may not be beveled, and instead be pointed or otherwise configured to penetrate the flaps 8 of the tissue structures 2, 4. Alternately, connectors 74 having different configurations may be used within a single anastomosis tool 30. The connectors 74 are initially independent from one another. That is, the connectors 74 are discrete and are not connected to one another prior to deployment, nor are they connected to one another after deployment. Alternately, at least two of the connectors 74 are initially connected to one another in a manner that allows them to separate from one another during deployment. For example, the connectors 74 may be connected to one another via thin strips of material configured to break during deployment. In this way, the connectors 74 may be more easily loaded into the tool 30, while still providing a compliant anastomosis with a plurality of independent connectors 74.

Each connector 74 initially may be positioned within or in proximity to a connector deployer 72. One example of a connector deployer 72 is an opening in a clamp 20. The connector deployer 72 may include one or more tracks 73. The tracks 73 are configured to at least partially receive the corresponding connector 74 and assist in holding the connector 74 in place before its use. Where the connector 74 is the staple described with regard to FIG. 18, at least one leg 204 is initially received in a track 73 of the connector deployer 72. Each connector 74 initially may be held in the corresponding connector deployer 72 via a friction fit against one or more of the tracks 73. Optionally, one or more of the connectors 74 is at least partially coated with sodium stearate, or a different biocompatible substance having similar properties. The sodium stearate assists in holding the coated connector 74 in place before deployment. Further, as the coated connector 74 begins to move out of the corresponding connector deployer 72, the sodium stearate serves as a lubricant to facilitate deployment of the connector 74. As shown the connector deployers 72 are simply passages between the channel 80 and a surface of the clamp 20. However, one or more of the connector deployers 72 may be configured differently.

As the trigger 286 is depressed, the crossbar 292 urges the actuator 78 distally. The actuator 78 is a piece of material that fits at least partially within the channel 80, and which is shaped at its distal end in such a way as, when it is urged distally, to cause the connector deployers 72 to deploy connectors 74. As shown in FIG. 14, the distal end 302 of the actuator 78 is angled relative to the longitudinal centerline of the channel 80. Each connector 74 may extend at least partially into the channel 80 before they are deployed, such that contact between the distal end 302 of the actuator 78 and a connector 74 urges the connector 74 through a connector deployer 72. However, the distal end 302 of the actuator 78 may be curved or shaped in another way, or the connector deployers 72 may be configured differently.

An anvil 304 is positioned on an arm 22, 24 of a clamp 20 opposite the arm 22, 24 of the other clamp 20 from which connectors 74 are deployed. An anvil 304 may be placed on both arms 22, 24 of a clamp 20; for example, where connectors 74 are deployed from both arms 22, 24 of the corresponding clamp 20. The anvil 304 may be metallic, or composed of another material against which the connectors 74 can be urged such that contact between the connectors 74 and the anvil 304 facilitates deployment of the connectors 74. The anvil 304 may be clipped onto the corresponding arm 22, 24 as shown, or may be formed into the arm 22, 24 or connected to the arm 22, 24 in a different way. Referring also to FIG. 12, one or more depressions 306 optionally may be formed into the surface of the anvil 304. The location of the depressions 306 corresponds to the location of the connector deployers 72 on the corresponding clamp 20. That is, the depressions 306 are positioned on the anvil 304 such that a connector 74 deployed through a connector deployer 72 in one clamp 20 contacts the depression 306 in the anvil 304.

The depression 306 is shaped to facilitate deployment of the connector 74. Referring also to FIG. 1, if the connector 74 is a staple, such as shown in FIGS. 18–19, the corresponding depression 306 is formed to direct the legs 204 of the staple in the desired directions to cause the staple to close and thereby hold the flaps 8 of the adjoining tissue structures 2, 4 together. The tissue structures and flaps are not shown for clarity. Both of the legs 204 are deflected inward toward one another substantially along a first dimension 212 that is substantially parallel to the longitudinal centerline of the base 202, due to contact with the depressions 306 of the anvil 302. The anvil 302 and depressions 306 may be as described above with reference to FIGS. 12 and 14, or may be different structures or mechanisms. The bevel surfaces 210 are oriented to facilitate this deflection. That is, contact between each bevel surface 210 of the staple and the corresponding depression 306 creates a moment that deflects the corresponding leg 204 of the staple in a desired direction. Further, at least partly as a result of the orientation of the bevel surfaces 210, the legs 204 do not substantially interfere with one another as they are deflected inward. Rather, the legs 204 additionally deflect in opposite directions substantially along a second dimension 214 that is substantially perpendicular to the first dimension 212, such that the legs 204 do not substantially interfere with one another. That is, the legs 204 slide past one another substantially without interference as the staple is deployed. Contact between the legs 204 that does not cause substantial interference therebetween may occur. That is, the bevel surfaces 210 are oriented such that contact between the bevel surfaces 210 and the depressions 306 of the anvil 302 results in deflection of the legs 204 toward another as well as lateral deflection of the legs 204 away from one another substantially along the second dimension 214. The connectors 74 may be plastically deformed during deployment. After the connector 74 is deployed, it connects adjacent flaps 8, and may be located such that it has limited or substantially no contact with the bloodstream. In this way, the risk of thrombosis is reduced.

As the crossbar 292 continues to rotate relative to the pin 288, it continues to engage the actuator 78 and urge it distally. As the actuator 78 continues to move distally, the actuator 78 sequentially urges each connector 74 through a corresponding connector deployer 72. That is, the actuator 78 contacts each connector 74 in sequence, from the most proximal connector 74 to the most distal connector 74. A different sequence may be utilized, if desired, with a corresponding change to the shape of the distal end 302 of the actuator 78 or the actuator 78 overall.

At least one actuator 78 continues to translate distally after all of the connectors 74 have been deployed. The flaps 8 are then freed from the clips 32. As one example, each clip 32 may be opened as a result of contact between an actuator 78 and the clip 32, or between the actuator 78 and a structure or mechanism connected to the clip. As another example, one or more tissue knives (not shown) moved by the actuator 78 may cut each flap 8 free from the associated clip 32, as described above with regard to the previous embodiment. One or more actuators 78 may include a keel 306 extending therefrom. The keel 306 extends through a first slot 81 in the arm 22, 24 in which the channel 80 is located. The first slot may open into the channel 80. After the clamps 20 have been brought together, the keel 306 also extends through a second slot 308 in an arm 22, 24 of the opposing clamp 20. The second slot 308 additionally extends through the anvil 304, if an anvil 304 is utilized. The second slot 308 opens into a second channel 270 in the arm 22, 24.

The second channel 270 is configured to allow the keel 306 to translate through it as the actuator 78 translates distally. As the actuator 78 translates distally after deploying the final connector 74, the keel 306 contacts the catch 262. The catch 262 is oriented such that the motion of the keel 306 moves the catch 262 out of engagement with the aperture 264. The tissue structure 2, 4 held within the clamps 20 acts to bias the clamps 20 from the closed position toward a more open position. Thus, when the tooth 266 of a catch 262 is free relative to the corresponding aperture 264, the first arm 22 and second arm 24 are urged apart, such that the catch 262 exits the aperture 264. The clamp 20 is then at least partially open, freeing the tissue structure 2, 4 held within that clamp 20. Similarly, at least one actuator 78 includes a segment 307 configured to engage a catch 262 within the channel 80 and move that catch 262 out of engagement with the corresponding aperture 264 as the actuator 78 translates distally after deploying the final connector, causing that clamp 20 to at least partially open. The tool 30 is then withdrawn from the anastomosis site. Where connectors 74 and corresponding connector deployers 72 are provided in more than one clamp 20, an actuator 78 is provided in each clamp 20. The actuators 78 need not have the same configuration or construction in each clamp 20.

Figure 15:
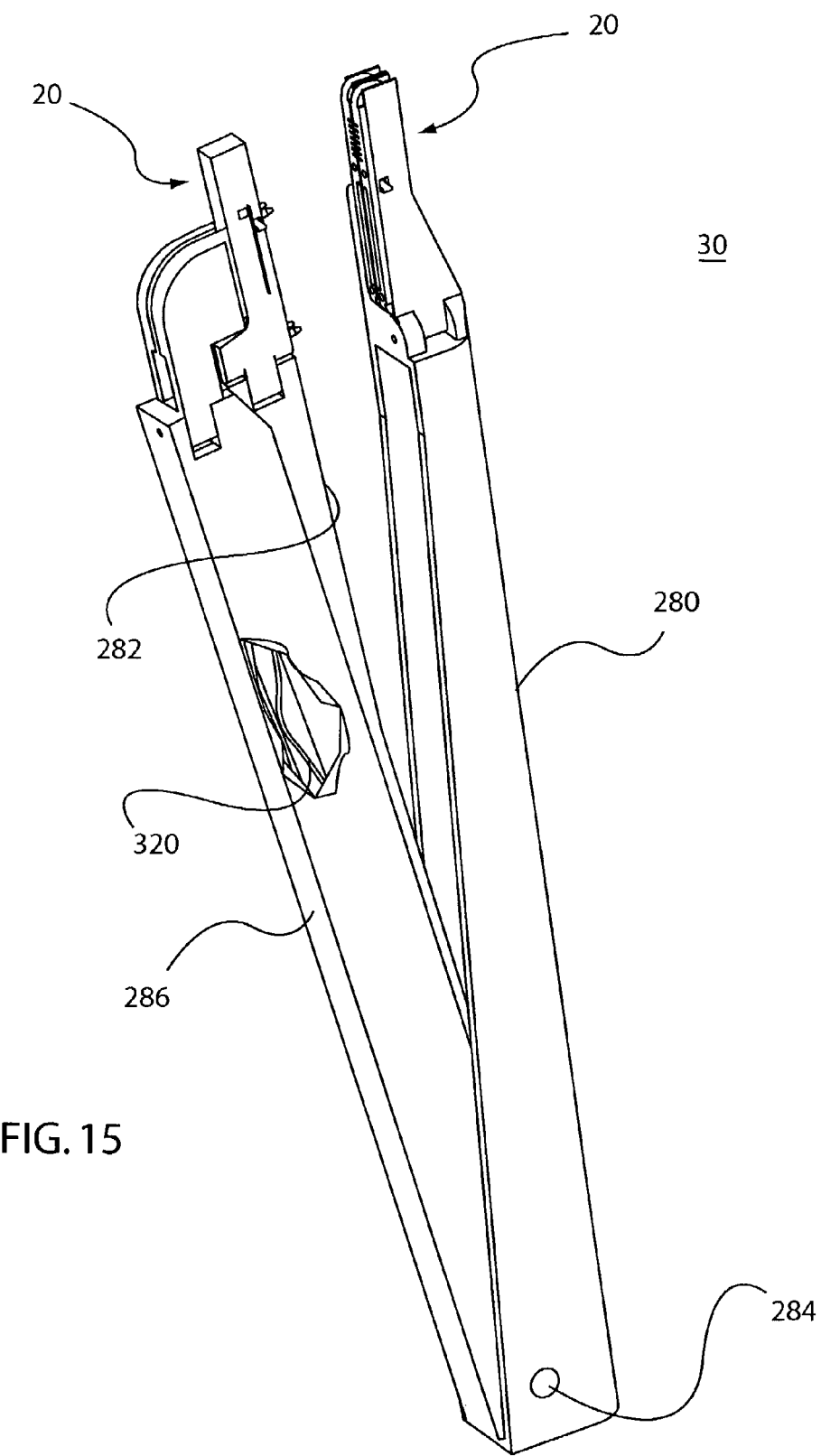
FIG. 15 is a perspective view of another embodiment of the anastomosis tool, partially cut away to show a biasing member therein.
Figure 16:
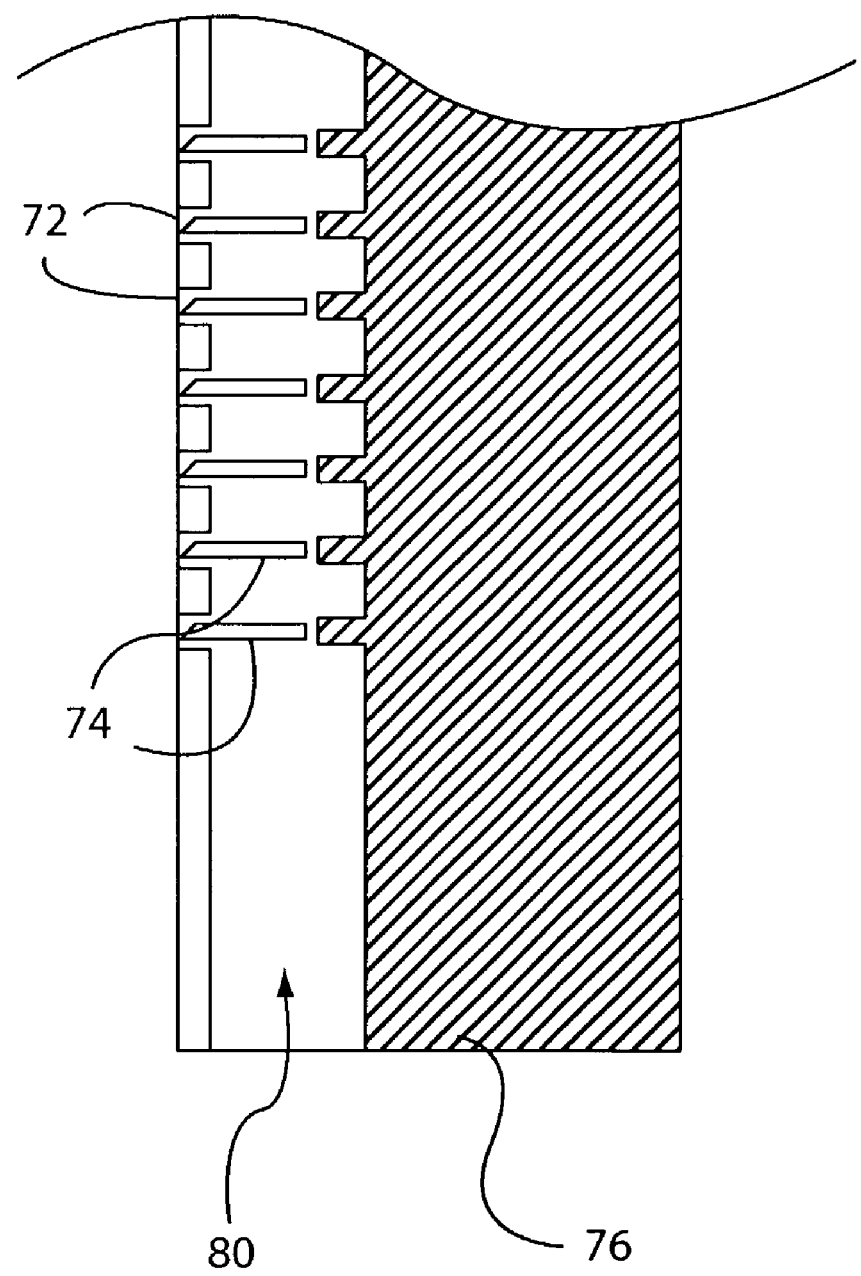
FIG. 16 is a cutaway view of a channel in the distal end of a clamp of the anastomosis tool of FIG. 15.

Referring to FIGS. 15–16, another embodiment of the anastomosis tool 30 is shown. In this embodiment, the actuator 78 is configured to deploy substantially all of the connectors 74 at the same time. As in the previous embodiment, the anastomosis tool 30 includes a first member 280 and a second member 282 that are movable relative to one another. The first member 280 and the second member 282 may be rotatable relative to one another about a pin 284 that may be fixed to one of the members 280, 282. As in the previous embodiment, a clamp 20 is connected to the distal end of each member 280, 282. Each clamp 20 may be connected to a different part of the corresponding member 280, 282, if desired.

The trigger 286 may be positioned on the opposite side of the second member 282 from the first member 280. Alternately, the trigger 286 is positioned on the opposite side of the first member 280 from the second member 282. The trigger 286 may also rotate about the pin 284, such that the members 280, 282 and the trigger 286 are all rotatable about one another. Alternately, the trigger 286 is connected to at least one of the members 280, 282 in a different way. The pad 290 may be omitted from the trigger 286. For example, the trigger 286 may be configured to be actuated by grasping it, rather than by applying force to it via a finger or thumb. A biasing member 320 is positioned between the trigger 286 and the second member 282. The biasing member 320 biases the trigger 286 away from the second member 282. The biasing member 320 is a leaf spring. However, the biasing member 320 may be any mechanism or structure capable of biasing the trigger 286 away from the second member 282.

As described above, each clamp 20 is closed onto a tissue structure 2, 4 when the anastomosis tool 30 is in the first position, in which the clamps 20 are spaced apart from one another. To actuate the anastomosis tool 30, the user squeezes the trigger 286 and the first member 280 toward one another. The biasing member 320 resists this compressive force, causing the first member 280 and the second member 282 to move closer to one another, while the trigger 286 does not move substantially relative to the second member 282. Referring also to FIG. 1, as the members 280, 282 move closer to one another, the clamps 20 are brought into position relative to one another such that the flaps 8 of one tissue structure 2 are brought into contact with the flaps 8 of the other tissue structure 4. The tissue structures 2, 4 and flaps 8 are not shown for clarity. The first member 280 and the second member 282 are configured such that they cannot substantially move any closer relative to one another after the flaps 8 of the tissue structures 2, 4 are pressed into contact with one another, at which point the anastomosis tool 30 is in a second position.

After the members 280, 282 have reached the second position, the user continues to exert force on the anastomosis tool 30 to move the trigger 286 toward the first member 280. This force acts against the biasing force exerted by the biasing element 320, and overcomes that biasing force. Thus, the trigger 286 moves closer to the second member 282.

Referring also to FIG. 16, the trigger 286 is directly connected to the actuator 78. The trigger 286 may be fixed to the actuator 78, or formed into a single unit with the actuator 78. Consequently, the crossbar 292 and the guards 298 of the previous embodiment need not be provided. The trigger 286 is oriented relative to the actuator 78 and the clamp 20 such that the motion of the trigger 286 relative to the second member 282 causes the actuator 78 to move within the channel 80 in a direction substantially parallel to the direction of deployment of the connectors 74. As described above, connectors 74 are positioned adjacent to the connector deployers 72. The actuator 78 is moved within the channel 80 to contact and deploy substantially all of the connectors 74 at substantially the same time. This deployment may be performed by substantially uniformly pushing all of the connectors 74 through the adjacent connector deployers 72. The connectors 74 may be deployed substantially as described above, completing the anastomosis. Alternately, an intermediate mechanism or structure may be placed between the actuator 78 and the connectors 74, if desired. If so, the actuator 78 contacts the intermediate mechanism or structure, which in turn urges one or more connectors 74 through the corresponding connector deployers 72. After the connectors 74 have been deployed, the trigger 286 is released, thereby allowing the biasing element 320 to bias the trigger 286 away from the second element 282. The members 280, 282 are then free to separate from another, and the anastomosis tool 30 can be removed from the anastomosis site.

Figure 17:
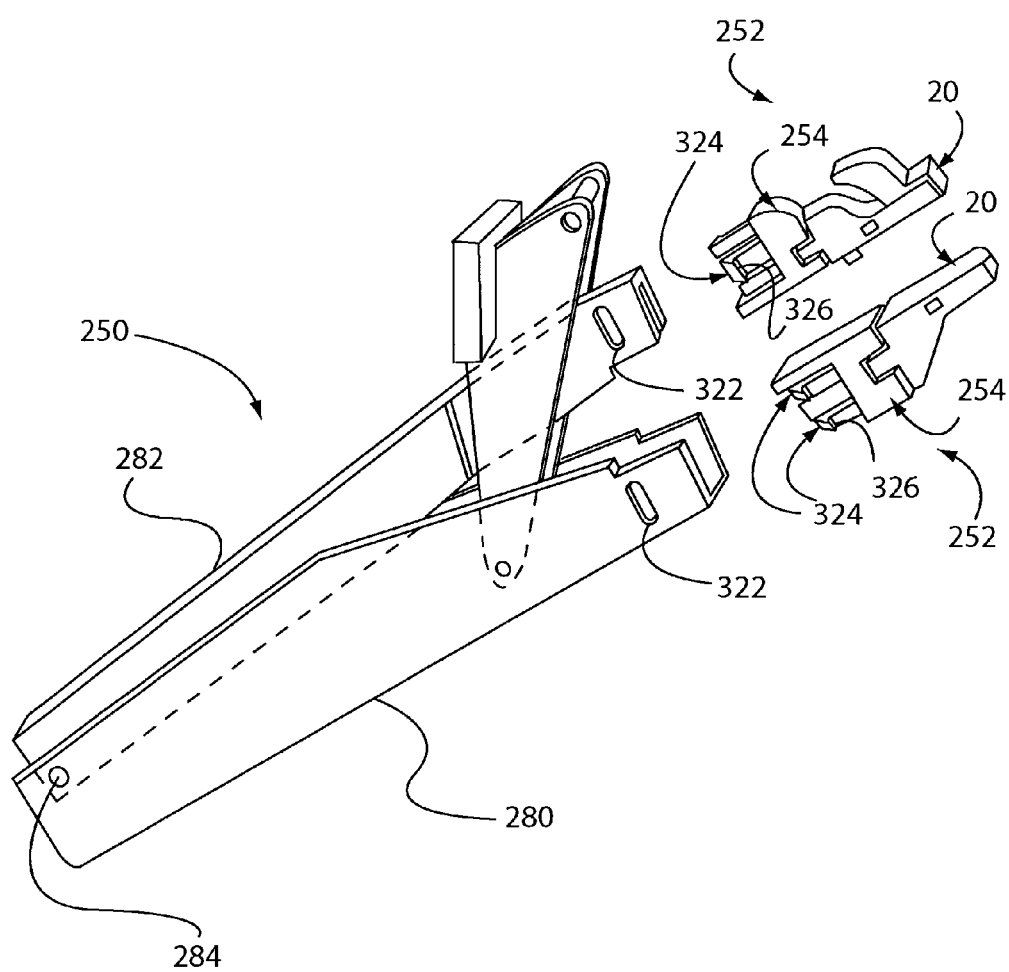
FIG. 17 is a perspective view of another embodiment of the anastomosis tool.

Referring to FIG. 17, in another embodiment, the anastomosis tool 30 includes a handle 250 and two cartridges 252 detachable from the handle 250. The handle 250 includes a first member 280 and a second member 282 that are movable relative to one another. The handle 250 may include a pin 284 that may be fixed to one of the members 280, 282, where the members 280, 282 are rotatable about the pin 284. The handle 250 is constructed from stainless steel or other durable material that can be sterilized after usage with a particular patient. Each cartridge 252 includes a clamp 20, which may be configured as described above. Alternately, the clamp 20 may be configured differently. Each cartridge 252 may include a proximal component 254 to which the clamp 20 is connected. The proximal component 254 is configured to interface with the handle 250. Where the pin 260 is used, the pin 260 may connect the clamp 20 to the proximal component 254.

The cartridges 252 are detachably connected to the handle 250. As one example, at least one aperture 322 may be defined in each member 280, 282 of the handle 250. As shown, each member 280, 282 has a substantially U-shaped cross-section, such that each aperture 322 extends completely through a portion of each member 280, 282. Each cartridge 252 includes at least one finger 324 corresponding to an aperture 322 in the corresponding member 280, 282. Each finger 324 is connected to the proximal component 254 of the cartridge 252. Alternately, one or more fingers 324 are connected to a different part of the connector 252. The finger 324 includes a tooth 326 at its proximal end. The teeth 326 extend outward to a distance wider than the width of at least part of the inner volume of the corresponding member 280, 282. As the cartridge 252 is inserted into the corresponding member 280, 282, the finger or fingers 324 initially flex inward, due to contact with the member 280, 282. Each finger 324 exerts a biasing force opposite the direction in which it is flexed, because the flexibility of each finger 324 has caused it to move away from a neutral position. As the cartridge 252 continues to move relative to the member 280, 282, the tooth 326 of each finger 324 eventually encounters the corresponding aperture 322. The finger 324 then flexes outward, pressing the tooth 326 into or through that aperture 322. The engagement between the teeth 326 of the cartridge 252 and the corresponding apertures 322 locks the cartridge 252 into place. However, the cartridges 252 may be detachably connected to the handle 250 in a different way. Further, each cartridge 252 each may be connected to the handle via a different structure or mechanism. The anastomosis tool 30 may then be operated as described above.

When an anastomosis is complete, each cartridge 252 can be removed by pressing the at least one tooth 326 of each cartridge 252 inward, out of engagement with the corresponding aperture 322. The cartridge 252 is then moved distally, and separated from the corresponding member 280, 282. The cartridges 252 may be disposable. That is, after each anastomosis, at least one cartridge 252 can be detached from the handle 250 and replaced with a new one. In this way, multiple anastomoses can be performed using a single handle 250.

The anastomosis tools 30 described above each deploy connectors 74 to form a compliant anastomosis. That is, the connectors 74 are independent from one another and spaced apart from one another, allowing the tissue structures 2, 4 to expand and contract at the location of the anastomosis.

The anastomosis tool 30 and connectors 74 described above may be used for endoscopic procedures or other surgical procedures. The anastomosis tool 30 additionally may be used to perform end-to-end anastomosis within a limited anatomical volume, such as within the cranium. The clamps 20 of the anastomosis tool 30 may be thin and/or elongated to allow the anastomosis tool 30 to access areas of the anatomy through small access ports, or to access limited anatomical volumes. Additionally, the handle 250 of the anastomosis tool similarly may be altered or configured to facilitate access to desired areas of the anatomy. Further, the anastomosis tool 30 is not restricted to human use, and may be used to perform anastomosis in other animals.

While the invention has been described in detail, it will be apparent to one skilled in the art that various changes and modifications can be made and equivalents employed, without departing from the present invention. It is to be understood that the invention is not limited to the details of construction and/or the arrangements of components set forth in the above description or illustrated in the drawings. Therefore, the invention is not to be restricted or limited except in accordance with the following claims and their legal equivalents.

What is claimed is:

1. A system for performing anastomosis between tissue structures, comprising:
    at least two clamps moveable relative to one another, wherein at least one said clamp comprises a first arm and a second arm moveably connected to one another; further comprising a catch extending from said first arm and a corresponding aperture defined in said second arm; wherein said catch is configured to engage said aperture to prevent said first and second arms from separating in use after said clamp is closed;
    a plurality of connectors detachably connected to at least one said clamp; and
    at least one actuator movable along a channel in at least one said arm to deploy, said connectors.

2. The system of claim 1, wherein said actuator is movable to deploy said connectors sequentially.

3. The system of claim 1, wherein said actuator is movable to deploy at least two said connectors substantially simultaneously.

4. The system of claim 1, wherein at least one said clamp further comprises a connector deployer corresponding to each said connector.

5. The system of claim 4, wherein at least one said connector deployer comprises at least one track, wherein said at least one track is configured to receive one of said connectors.

6. The system of claim 4, wherein at least one said connector is at least partially coated with sodium stearate.

7. The system of claim 4, wherein at least one said clamp comprises a first channel defined therein, said actuator configured to translate at least partially through said channel, wherein at least one said connector deployer intersects said first channel.

8. The system of claim 7, wherein at least one said connector extends at least partially into said first channel before deployment.

9. The system of claim 4, further comprising at least one anvil connected to at least one said clamp.

10. The system of claim 9, further comprising a plurality of depressions on said anvil, said depressions corresponding to said connector deployers.

11. The system of claim 1, wherein at least two of said connectors initially are detachably connected to one another.

12. The system of claim 1, further comprising a second channel defined in said second arm, wherein said actuator further comprises a keel movable at least partially within said second channel.

13. The system of claim 12, wherein said actuator is moveable distally, and wherein said keel is configured to urge said catch out of engagement with said aperture when said actuator has moved a predetermined amount.

14. A system for performing anastomosis between tissue structures, comprising:
    a handle;
    at least two clamps connected to said handle and moveable relative to one another, wherein at least one said clamp is detachable from said handle; and wherein at least one said clamp comprises a first arm and a second arm moveably connected to one another; further comprising a catch extending from said first arm; and a corresponding aperture defined in said second arm, wherein said catch is configured to engage said aperture to prevent said first and second arms from separating in use after said clamp is closed;
    a plurality of connectors detachably connected to at least one said clamp; and
    at least one actuator movable along a channel in at least one said arm.

15. A system for performing anastomosis between tissue structures, comprising:
    at least two clamps moveable relative to one another;
    a plurality of connectors detachably connected to at least one said clamp; wherein at least one said connector is at least partially coated with sodium stearate; and
    at least one actuator slidable along a channel in at least one said clamp to deploy at least one said connector.

* * * * *